(12) United States Patent
Guan et al.

(10) Patent No.: US 10,081,827 B2
(45) Date of Patent: *Sep. 25, 2018

(54) MAPPING CYTOSINE MODIFICATIONS

(71) Applicant: New England Biolabs, Inc., Ipswich, MA (US)

(72) Inventors: Shengxi Guan, Stoneham, MA (US); Nan Dai, Gloucester, MA (US); Zhenyu Zhu, Beverly, MA (US); Ivan R. Correa, Jr., Ipswich, MA (US); Aine Quimby, Newton, NH (US); Janine Borgaro, Beverly, MA (US)

(73) Assignee: New England Biolabs, Inc., Ipswich, MA (US)

( * ) Notice: Subject to any disclaimer, the term of this patent is extended or adjusted under 35 U.S.C. 154(b) by 309 days.

This patent is subject to a terminal disclaimer.

(21) Appl. No.: 14/993,590

(22) Filed: Jan. 12, 2016

(65) Prior Publication Data
US 2016/0138079 A1    May 19, 2016

Related U.S. Application Data

(63) Continuation-in-part of application No. 13/826,395, filed on Mar. 14, 2013, now Pat. No. 9,267,117.

(60) Provisional application No. 61/724,041, filed on Nov. 8, 2012, provisional application No. 61/723,427, filed on Nov. 7, 2012, provisional application No. 61/722,968, filed on Nov. 6, 2012, provisional application No. 61/611,295, filed on Mar. 15, 2012.

(51) Int. Cl.
| | |
|---|---|
| *C12Q 1/68* | (2018.01) |
| *C12N 9/10* | (2006.01) |
| *C12N 9/02* | (2006.01) |
| *C12P 19/30* | (2006.01) |
| *C12P 19/18* | (2006.01) |
| *C12N 9/22* | (2006.01) |
| *C12P 19/34* | (2006.01) |
| *C12Q 1/6827* | (2018.01) |

(52) U.S. Cl.
CPC ............ *C12Q 1/68* (2013.01); *C12N 9/0069* (2013.01); *C12N 9/0071* (2013.01); *C12N 9/1048* (2013.01); *C12N 9/1051* (2013.01); *C12N 9/22* (2013.01); *C12P 19/18* (2013.01); *C12P 19/30* (2013.01); *C12P 19/34* (2013.01); *C12Q 1/6827* (2013.01); *C12Y 114/11* (2013.01)

(58) Field of Classification Search
CPC ........................................................ C12Q 1/68
See application file for complete search history.

(56) References Cited

U.S. PATENT DOCUMENTS

| | | |
|---|---|---|
| 2012/0301881 A1 | 11/2012 | Zhu et al. |
| 2013/0244237 A1 | 9/2013 | Vaisvila et al. |

FOREIGN PATENT DOCUMENTS

| | | |
|---|---|---|
| WO | WO20100037001 | 4/2010 |
| WO | WO2011025819 | 3/2011 |
| WO | WO2011091146 | 7/2011 |
| WO | WO2011127136 | 10/2011 |

OTHER PUBLICATIONS

Terragni et al. (Biochemical Characterization of Recombinant β-Glucosyltransferase and Analysis of Global 5-Hydroxymethylcytosine in Unique Genomes, Biochemistry, 51, 1009-1019, published on Jan. 9, 2012).*
Borgaro et al Nucleic Acids Res. 2013 41: 4198-4206.
Wang et al Nucleic Acids Res. 2011 39: 9294-305.
Adams et al J. Bacteriol. 2008 190, 8053-8064.
Moréra et al J. Mol. Biol. 2001 311:569-77.
Moréra et al J. Mol. Biol. 1999 292:717-30.
Ito et al Science. 2011 333: 1300-3.
Wu et al Genes Dev. 2011 25: 2436-52.
Williams et al EMBO Rep. 2012 13:28-35.
Hashimoto et al Nature. 2014 506: 391-5.
Saleh et al FASEB Journal 2014 28 Supplement 768.16.
International Search Report for International Application No. PCT/US2013/068290 dated Mar. 11, 2014.
Szwagierczak, et al, Nucleic Acids Research, 19, e-181, 2010.
Li, et al., Chemistry and Biology, 11, 1, 107-119, 2004.
Seto, et al., Eur. J. Biochem, 259, 3, 770-775, 1999.
Song, et al., Nature Biotechnology, 29, 1, 68-72, 2011.
Yu, et al., Cell, 149, 6, 1368-1380, 2012.
Yu, et al., Nature Protocols, 7, 12, 2159-2170, 2012.
Borgaro, et al., Nucleic Acids Research, 41(5):1-9 (2013).
Booth, et al., Science, 336:934-937 (2012).
Jagdale, et al., Synthesis, 4:660-664 (2009).
Morales-Serna, et al., Synthesis, 9:1375-1382 (2011).
Falorni, et al., Tetrahedron Lett., 40: 4395-4396 (1999).

* cited by examiner

*Primary Examiner* — Suzanne M Noakes
*Assistant Examiner* — Jae W Lee
(74) *Attorney, Agent, or Firm* — New England Biolabs, Inc; Harriet M. Strimpel

(57) ABSTRACT

Methods, compositions and kits for selectively altering and detecting modified cytosine residues are provided.

9 Claims, 8 Drawing Sheets
Specification includes a Sequence Listing.

T4-BGT

5-β-gmC

5-β-2-gNmC

5-β-6-gNmC

5-β-6-N₃-gmC

T4-BGT FOLLOWED BY T6-BGAGT

5-β,α-ggmC

5-β-2-gN-α-gmC

5-β-6-gN-α-gmC

5-β-6-N₃-α-gmC

EXCLUSIVE mC MAPPING

EXCLUSIVE fC MAPPING

EXCLUSIVE caC MAPPING

SEQUENCE LISTING

```
<160> NUMBER OF SEQ ID NOS: 14

<210> SEQ ID NO 1
<211> LENGTH: 351
<212> TYPE: PRT
<213> ORGANISM: Bacteriophage T4

<400> SEQUENCE: 1

Met Lys Ile Ala Ile Ile Asn Met Gly Asn Asn Val Ile Asn Phe Lys
1               5                   10                  15

Thr Val Pro Ser Ser Glu Thr Ile Tyr Leu Phe Lys Val Ile Ser Glu
            20                  25                  30

Met Gly Leu Asn Val Asp Ile Ile Ser Leu Lys Asn Gly Val Tyr Thr
        35                  40                  45

Lys Ser Phe Asp Glu Val Asp Val Asn Asp Tyr Asp Arg Leu Ile Val
    50                  55                  60

Val Asn Ser Ser Ile Asn Phe Phe Gly Gly Lys Pro Asn Leu Ala Ile
65                  70                  75                  80

Leu Ser Ala Gln Lys Phe Met Ala Lys Tyr Lys Ser Lys Ile Tyr Tyr
                85                  90                  95

Leu Phe Thr Asp Ile Arg Leu Pro Phe Ser Gln Ser Trp Pro Asn Val
            100                 105                 110

Lys Asn Arg Pro Trp Ala Tyr Leu Tyr Thr Glu Glu Glu Leu Leu Ile
        115                 120                 125
```

```
Lys Ser Pro Ile Lys Val Ile Ser Gln Gly Ile Asn Leu Asp Ile Ala
    130                 135                 140
Lys Ala Ala His Lys Lys Val Asp Asn Val Ile Glu Phe Glu Tyr Phe
145                 150                 155                 160
Pro Ile Glu Gln Tyr Lys Ile His Met Asn Asp Phe Gln Leu Ser Lys
                165                 170                 175
Pro Thr Lys Lys Thr Leu Asp Val Ile Tyr Gly Gly Ser Phe Arg Ser
            180                 185                 190
Gly Gln Arg Glu Ser Lys Met Val Glu Phe Leu Phe Asp Thr Gly Leu
        195                 200                 205
Asn Ile Glu Phe Phe Gly Asn Ala Arg Glu Lys Gln Phe Lys Asn Pro
    210                 215                 220
Lys Tyr Pro Trp Thr Lys Ala Pro Val Phe Thr Gly Lys Ile Pro Met
225                 230                 235                 240
Asn Met Val Ser Glu Lys Asn Ser Gln Ala Ile Ala Ala Leu Ile Ile
                245                 250                 255
Gly Asp Lys Asn Tyr Asn Asp Asn Phe Ile Thr Leu Arg Val Trp Glu
            260                 265                 270
Thr Met Ala Ser Asp Ala Val Met Leu Ile Asp Glu Glu Phe Asp Thr
        275                 280                 285
Lys His Arg Ile Ile Asn Asp Ala Arg Phe Tyr Val Asn Asn Arg Ala
    290                 295                 300
Glu Leu Ile Asp Arg Val Asn Glu Leu Lys His Ser Asp Val Leu Arg
305                 310                 315                 320
Lys Glu Met Leu Ser Ile Gln His Asp Ile Leu Asn Lys Thr Arg Ala
                325                 330                 335
Lys Lys Ala Glu Trp Gln Asp Ala Phe Lys Lys Ala Ile Asp Leu
            340                 345                 350

<210> SEQ ID NO 2
<211> LENGTH: 400
<212> TYPE: PRT
<213> ORGANISM: Bacteriophage T4

<400> SEQUENCE: 2

Met Arg Ile Cys Ile Phe Met Ala Arg Gly Leu Glu Gly Cys Gly Val
1               5                   10                  15
Thr Lys Phe Ser Leu Glu Gln Arg Asp Trp Phe Ile Lys Asn Gly His
            20                  25                  30
Glu Val Thr Leu Val Tyr Ala Lys Asp Lys Ser Phe Thr Arg Thr Ser
        35                  40                  45
Ser His Asp His Lys Ser Phe Ser Ile Pro Val Ile Leu Ala Lys Glu
    50                  55                  60
Tyr Asp Lys Ala Leu Lys Leu Val Asn Asp Cys Asp Ile Leu Ile Ile
65                  70                  75                  80
Asn Ser Val Pro Ala Thr Ser Val Gln Glu Ala Thr Ile Asn Asn Tyr
                85                  90                  95
Lys Lys Leu Leu Asp Asn Ile Lys Pro Ser Ile Arg Val Val Val Tyr
            100                 105                 110
Gln His Asp His Ser Val Leu Ser Leu Arg Arg Asn Leu Gly Leu Glu
        115                 120                 125
Glu Thr Val Arg Arg Ala Asp Val Ile Phe Ser His Ser Asp Asn Gly
    130                 135                 140
Asp Phe Asn Lys Val Leu Met Lys Glu Trp Tyr Pro Glu Thr Val Ser
145                 150                 155                 160
```

Leu Phe Asp Asp Ile Glu Ala Pro Thr Val Tyr Asn Phe Gln Pro
            165                 170                 175

Pro Met Asp Ile Val Lys Val Arg Ser Thr Tyr Trp Lys Asp Val Ser
        180                 185                 190

Glu Ile Asn Met Asn Ile Asn Arg Trp Ile Gly Arg Thr Thr Thr Trp
            195                 200                 205

Lys Gly Phe Tyr Gln Met Phe Asp Phe His Glu Lys Phe Leu Lys Pro
        210                 215                 220

Ala Gly Lys Ser Thr Val Met Glu Gly Leu Glu Arg Ser Pro Ala Phe
225                 230                 235                 240

Ile Ala Ile Lys Glu Lys Gly Ile Pro Tyr Glu Tyr Tyr Gly Asn Arg
            245                 250                 255

Glu Ile Asp Lys Met Asn Leu Ala Pro Asn Gln Pro Ala Gln Ile Leu
        260                 265                 270

Asp Cys Tyr Ile Asn Ser Glu Met Leu Glu Arg Met Ser Lys Ser Gly
        275                 280                 285

Phe Gly Tyr Gln Leu Ser Lys Leu Asn Gln Lys Tyr Leu Gln Arg Ser
        290                 295                 300

Leu Glu Tyr Thr His Leu Glu Leu Gly Ala Cys Gly Thr Ile Pro Val
305                 310                 315                 320

Phe Trp Lys Ser Thr Gly Glu Asn Leu Lys Phe Arg Val Asp Asn Thr
            325                 330                 335

Pro Leu Thr Ser His Asp Ser Gly Ile Ile Trp Phe Asp Glu Asn Asp
        340                 345                 350

Met Glu Ser Thr Phe Glu Arg Ile Lys Glu Leu Ser Ser Asp Arg Ala
        355                 360                 365

Leu Tyr Asp Arg Glu Arg Glu Lys Ala Tyr Glu Phe Leu Tyr Gln His
        370                 375                 380

Gln Asp Ser Ser Phe Cys Phe Lys Glu Gln Phe Asp Ile Ile Thr Lys
385                 390                 395                 400

<210> SEQ ID NO 3
<211> LENGTH: 321
<212> TYPE: PRT
<213> ORGANISM: Acinetobacter baumannii

<400> SEQUENCE: 3

Leu Cys Asn Lys Ala Ser Ser Asp Leu Thr Asp Tyr Val Ile Arg Gln
1               5                   10                  15

Leu Gly Arg Thr Lys Asn Lys Arg Tyr Glu Ala Tyr Val Val Ser Arg
            20                  25                  30

Ile Ile His Leu Leu Asn Asp Phe Thr Leu Lys Phe Val Thr Gln Gln
        35                  40                  45

Phe Val Arg Leu Ser Asn Lys Lys Ile Ala Leu Thr Asp Leu Tyr Phe
50                  55                  60

Pro Gln Leu Gly Ile His Ile Glu Val Asp Glu Gly His His Phe Leu
65                  70                  75                  80

Arg Asn Ser Lys Met Glu Tyr Ser Leu Asn Gln Ile Asp Glu Pro Leu
            85                  90                  95

Tyr Ser Ile Ser Gln Thr Glu Ser Asp Ala Met Arg Glu Glu Asp Ile
        100                 105                 110

Ile Ser Ile Thr Gly His Lys Ile Phe Arg Val Asn Val Phe Lys Asn
        115                 120                 125

Gln Glu Gly Gln Pro Gln Asn Leu Glu Asn Ile His Gln Gln Ile Asp

```
                130                 135                 140
Lys Ile Ile Glu Glu Ile Lys Thr Ala Lys Asn Lys Leu Ile Glu Ala
145                 150                 155                 160

Ser Thr Phe Lys Glu Trp Asn Ile Glu Thr Glu Tyr Asn Pro Gln Thr
                165                 170                 175

Tyr Ile Asp Leu Gly Arg Ile Ser Leu Ala Asp Asn Val Val Leu Lys
                180                 185                 190

Thr Thr Lys Asp Val Cys Asn Cys Phe Gly Tyr Ser Tyr Lys Asn Tyr
            195                 200                 205

Gln Arg Gly Gly Ala Leu His Pro Tyr Lys Lys Asp Thr Leu Ile Trp
210                 215                 220

Phe Pro Arg Leu Tyr Glu Asn Lys Asp Trp Ile Asn Thr Ile Ser Pro
225                 230                 235                 240

Asp Gly Leu Thr Ile Thr Glu Lys Ser Thr Asp Glu Thr Ile Thr Leu
                245                 250                 255

Lys Lys Leu Glu Glu Trp Lys Asn Gly Pro Gln Lys Arg Ile Val Phe
                260                 265                 270

Ala Arg Val Lys Asp Asn Leu Ser Ser Arg Ala Met Tyr Arg Phe Met
            275                 280                 285

Gly Leu Tyr Glu Phe Gln Lys Ala Asp Leu Lys Asp Gly Ala Val Trp
                290                 295                 300

Lys Arg Val Lys Cys Glu Val Gln Thr Tyr Ser Pro Lys Glu Thr Lys
305                 310                 315                 320

Cys
```

<210> SEQ ID NO 4
<211> LENGTH: 318
<212> TYPE: PRT
<213> ORGANISM: Acinetobacter baumannii

<400> SEQUENCE: 4

```
Met Phe Ser Ser Asp Leu Thr Asp Tyr Val Ile Arg Gln Leu Gly Arg
1               5                   10                  15

Thr Lys Asn Lys Arg Tyr Glu Ala Tyr Val Val Ser Arg Ile Ile His
            20                  25                  30

Leu Leu Asn Asp Phe Thr Leu Lys Phe Val Thr Gln Gln Phe Val Arg
        35                  40                  45

Leu Ser Asn Lys Lys Ile Ala Leu Thr Asp Leu Tyr Phe Pro Gln Leu
    50                  55                  60

Gly Ile His Ile Glu Val Asp Glu Glu His His Phe Leu Arg Asn Ser
65                  70                  75                  80

Lys Met Glu Tyr Ser Leu Asn Gln Ile Asp Glu Pro Leu Tyr Ser Ile
                85                  90                  95

Ser His Thr Glu Ser Asp Ala Met Arg Glu Glu Asp Ile Ile Ser Ile
            100                 105                 110

Thr Gly His Lys Ile Phe Arg Val Asn Val Phe Lys Asn Gln Glu Gly
        115                 120                 125

Gln Pro Gln Asn Leu Glu Ser Ile His Gln Ile Asp Lys Ile Ile
130                 135                 140

Glu Lys Ile Lys Thr Ala Lys Asn Lys Leu Ile Glu Ala Ser Thr Phe
145                 150                 155                 160

Lys Glu Trp Asn Ile Glu Thr Glu Tyr Asn Pro Gln Thr Tyr Ile Asp
                165                 170                 175

Leu Gly Arg Ile Ser Leu Ala Asp Asn Val Val Leu Lys Thr Thr Lys
```

```
                  180                 185                 190
Asp Val Cys Asn Cys Phe Gly Tyr Asn Tyr Lys Asn Tyr Gln Arg Gly
                195                 200                 205
Gly Ala Leu His Pro Tyr Glu Lys Asp Thr Leu Ile Trp Phe Pro Arg
            210                 215                 220
Leu Tyr Glu Asn Lys Asp Trp Phe Asn Thr Ile Ser Pro Asp Gly Leu
225                 230                 235                 240
Thr Ile Thr Glu Lys Ser Thr Asp Glu Ala Ile Thr Leu Lys Lys Leu
                245                 250                 255
Glu Glu Trp Lys Asn Gly Pro Gln Lys Arg Ile Val Phe Ala Arg Val
            260                 265                 270
Lys Asp Asn Leu Ser Ser Arg Ala Met Tyr Arg Phe Met Gly Leu Tyr
                275                 280                 285
Glu Phe Gln Lys Ala Asp Leu Lys Asp Gly Ala Val Trp Lys Arg Val
            290                 295                 300
Glu Cys Glu Val Gln Thr Tyr Ser Pro Lys Glu Thr Lys Cys
305                 310                 315

<210> SEQ ID NO 5
<211> LENGTH: 318
<212> TYPE: PRT
<213> ORGANISM: Acinetobacter baumannii

<400> SEQUENCE: 5

Met Phe Ser Ser Asp Leu Thr Asp Tyr Val Ile Arg Gln Leu Gly Arg
1               5                   10                  15
Thr Lys Asn Lys Arg Tyr Glu Ala Tyr Val Val Ser Arg Ile Ile His
            20                  25                  30
Leu Leu Asn Asp Phe Thr Leu Lys Phe Val Thr Gln Gln Phe Val Arg
        35                  40                  45
Leu Ser Asn Lys Lys Ile Ala Leu Thr Asp Leu Tyr Phe Pro Gln Leu
    50                  55                  60
Gly Ile His Ile Glu Val Asp Glu Gly His His Phe Leu Arg Asn Ser
65                  70                  75                  80
Lys Met Glu Tyr Ser Leu Asn Gln Ile Asp Pro Leu Tyr Ser Ile
                85                  90                  95
Ser Gln Thr Glu Ser Asp Ala Met Arg Glu Glu Asp Ile Ile Ser Ile
            100                 105                 110
Thr Gly His Lys Ile Phe Arg Val Asn Val Phe Lys Asn Gln Glu Gly
        115                 120                 125
Gln Pro Gln Asn Leu Glu Ser Ile His Gln Gln Ile Asp Lys Ile Ile
    130                 135                 140
Glu Glu Ile Lys Thr Ala Lys Asn Lys Leu Ile Glu Ala Ser Thr Phe
145                 150                 155                 160
Lys Glu Trp Asn Ile Glu Thr Glu Tyr Asn Pro Gln Thr Tyr Ile Asp
                165                 170                 175
Leu Gly Arg Ile Ser Leu Ala Asp Asn Val Val Leu Lys Thr Thr Lys
            180                 185                 190
Asp Val Cys Asn Cys Phe Gly Tyr Asn Tyr Lys Asn Tyr Gln Arg Gly
        195                 200                 205
Gly Ala Leu His Pro Tyr Glu Lys Asp Thr Leu Ile Trp Phe Pro Arg
    210                 215                 220
Leu Tyr Glu Asn Lys Asp Trp Ile Asn Thr Ile Ser Pro Asp Gly Leu
225                 230                 235                 240
```

```
Thr Ile Thr Glu Lys Ser Thr Asp Glu Thr Ile Thr Leu Lys Lys Leu
                    245                 250                 255

Glu Glu Trp Lys Asn Gly Pro Gln Lys Arg Ile Val Phe Ala Arg Val
            260                 265                 270

Lys Asp Asn Leu Ser Ser Arg Ala Met Tyr Arg Phe Met Gly Leu Tyr
                275                 280                 285

Glu Phe Gln Lys Ala Asp Leu Lys Asp Gly Ala Val Trp Lys Arg Val
            290                 295                 300

Lys Cys Glu Val Gln Thr Tyr Ser Pro Lys Glu Thr Lys Cys
305                 310                 315

<210> SEQ ID NO 6
<211> LENGTH: 318
<212> TYPE: PRT
<213> ORGANISM: Acinetobacter baumannii

<400> SEQUENCE: 6

Met Phe Ser Ser Asp Leu Thr Asp Tyr Val Ile Arg Gln Leu Gly Arg
1               5                   10                  15

Thr Lys Asn Lys Arg Tyr Glu Thr Tyr Val Val Ser Arg Ile Ile His
                20                  25                  30

Leu Leu Asn Asp Phe Thr Leu Lys Phe Val Thr Gln Gln Phe Val Arg
            35                  40                  45

Leu Ser Asn Lys Lys Ile Ala Leu Thr Asp Leu Tyr Phe Pro Gln Leu
50                  55                  60

Gly Ile His Ile Glu Val Asp Glu Glu His His Phe Leu Arg Asn Ser
65                  70                  75                  80

Lys Met Glu Tyr Ser Leu Asn Gln Ile Asp Glu Pro Leu Tyr Ser Ile
                85                  90                  95

Ser His Thr Glu Ser Asp Ala Met Arg Glu Asp Ile Ile Ser Ile
                100                 105                 110

Thr Gly His Lys Ile Phe Arg Val Asn Val Phe Lys Asn Gln Glu Gly
            115                 120                 125

Gln Pro Gln Asn Leu Glu Ser Ile His Gln Ile Asp Lys Ile Ile
130                 135                 140

Glu Glu Ile Lys Thr Ala Lys Asn Lys Leu Ile Glu Ala Ser Thr Phe
145                 150                 155                 160

Lys Glu Trp Asn Ile Glu Thr Glu Tyr Asn Pro Gln Thr Tyr Ile Asp
                165                 170                 175

Leu Gly Arg Ile Ser Leu Ala Asp Asn Val Val Leu Lys Thr Thr Lys
            180                 185                 190

Asp Val Cys Asn Cys Phe Gly Tyr Asn Tyr Lys Asn Tyr Gln Arg Gly
                195                 200                 205

Gly Ala Leu His Pro Tyr Lys Lys Asp Thr Leu Ile Trp Phe Pro Arg
            210                 215                 220

Leu Tyr Glu Asn Lys Asp Trp Ile Asn Thr Ile Ser Pro Asp Gly Leu
225                 230                 235                 240

Thr Ile Thr Glu Lys Ser Thr Asp Glu Thr Ile Thr Leu Lys Lys Leu
                245                 250                 255

Glu Glu Trp Lys Asn Gly Pro Gln Lys Arg Ile Val Phe Ala Arg Val
            260                 265                 270

Lys Asp Asn Leu Ser Ser Arg Ala Met Tyr Arg Phe Met Gly Leu Tyr
                275                 280                 285

Glu Phe Gln Lys Ala Asp Leu Lys Asp Gly Ala Val Trp Lys Arg Val
            290                 295                 300
```

```
Glu Cys Glu Val Gln Thr Tyr Ser Pro Lys Glu Thr Lys Cys
305                 310                 315
```

<210> SEQ ID NO 7
<211> LENGTH: 268
<212> TYPE: PRT
<213> ORGANISM: Acinetobacter baumannii

<400> SEQUENCE: 7

```
Ile Cys Arg Val Gln Arg Thr Asp Leu Tyr Phe Pro Gln Leu Gly Ile
1               5                   10                  15

His Ile Glu Val Asp Glu Gly His His Phe Leu Arg Asn Ser Lys Met
            20                  25                  30

Glu Tyr Ser Leu Asn Gln Ile Asp Glu Pro Leu Tyr Ser Ile Ser Gln
        35                  40                  45

Thr Glu Ser Asp Ala Met Arg Glu Glu Asp Ile Ile Ser Ile Thr Gly
    50                  55                  60

His Lys Ile Phe Arg Val Asn Val Tyr Lys Asn Gln Glu Gly Gln Pro
65                  70                  75                  80

Gln Asn Leu Glu Ser Ile His Gln Gln Ile Asp Lys Ile Ile Glu Glu
                85                  90                  95

Ile Lys Thr Ala Lys Asn Lys Leu Ile Glu Ala Ser Thr Phe Lys Glu
            100                 105                 110

Trp Asn Ile Glu Thr Glu Tyr Asn Pro Gln Thr Tyr Ile Asn Leu Gly
        115                 120                 125

Arg Ile Ser Leu Ala Asp Asn Val Val Leu Lys Thr Thr Lys Asp Val
    130                 135                 140

Cys Asn Cys Phe Gly Tyr Asn Tyr Lys Asn Tyr Gln Arg Gly Gly Ala
145                 150                 155                 160

Ile His Pro Tyr Glu Glu Asp Thr Leu Ile Trp Phe Pro Arg Leu Tyr
                165                 170                 175

Glu Asn Lys Asp Trp Ile Asn Thr Ile Ser Pro Asp Gly Leu Thr Ile
            180                 185                 190

Thr Glu Lys Ser Thr Asp Glu Thr Ile Thr Leu Lys Lys Leu Glu Glu
        195                 200                 205

Trp Lys Asn Gly Pro Gln Lys Arg Ile Val Phe Ala Arg Val Lys Asp
    210                 215                 220

Asn Leu Asn Ser Arg Ala Met Tyr Arg Phe Met Gly Leu Tyr Lys Phe
225                 230                 235                 240

Gln Lys Ala Asp Leu Lys Asp Gly Ala Val Trp Lys Arg Val Glu Cys
                245                 250                 255

Glu Val Gln Thr Tyr Ser Pro Lys Glu Thr Lys Cys
            260                 265
```

<210> SEQ ID NO 8
<211> LENGTH: 318
<212> TYPE: PRT
<213> ORGANISM: Acinetobacter baumannii

<400> SEQUENCE: 8

```
Met Phe Ser Ser Asp Leu Thr Asp Tyr Val Ile Arg Gln Leu Gly Arg
1               5                   10                  15

Thr Lys Asn Lys Arg Tyr Glu Ala Tyr Val Val Ser Arg Ile Ile His
            20                  25                  30

Leu Leu Asn Asp Ile Thr Leu Lys Phe Val Thr Gln Gln Phe Val Arg
        35                  40                  45
```

```
Leu Ser Asn Lys Lys Ile Ala Leu Thr Asp Leu Tyr Phe Pro Gln Leu
     50                  55                  60

Gly Ile His Ile Glu Val Asp Glu Gly His His Phe Leu Arg Asn Ser
 65                  70                  75                  80

Lys Met Glu Tyr Ser Leu Asn Gln Ile Asp Glu Pro Leu Tyr Ser Ile
                 85                  90                  95

Ser Gln Thr Glu Ser Asp Ala Met Arg Glu Glu Asp Ile Ile Ser Ile
            100                 105                 110

Thr Glu His Lys Ile Phe Arg Val Asn Val Tyr Lys Asn Gln Glu Gly
        115                 120                 125

Gln Pro Gln Asn Leu Glu Ser Ile His Gln Ile Asp Lys Ile Ile
    130                 135                 140

Glu Glu Ile Lys Thr Ala Lys Asn Lys Leu Val Glu Phe Lys Phe
145                 150                 155                 160

Lys Glu Trp Asn Ile Glu Thr Glu Tyr Asn Pro Gln Thr Tyr Ile Asp
                165                 170                 175

Leu Gly Arg Ile Ser Leu Ala Asp Asn Val Val Leu Lys Thr Thr Lys
            180                 185                 190

Asp Val Cys Asn Cys Phe Gly Tyr Asn Tyr Lys Asn Tyr Gln Arg Gly
        195                 200                 205

Gly Ala Leu His Pro Tyr Glu Lys Asp Thr Leu Ile Trp Phe Pro Arg
    210                 215                 220

Leu Tyr Glu Asn Lys Asp Trp Ile Asn Thr Ile Ser Pro Asp Gly Leu
225                 230                 235                 240

Thr Ile Thr Glu Lys Ser Thr Asp Glu Thr Ile Thr Leu Lys Lys Leu
                245                 250                 255

Glu Glu Trp Lys Asn Gly Pro Gln Lys Arg Ile Val Phe Ala Arg Val
            260                 265                 270

Lys Asp Asn Leu Ser Ser Arg Ala Met Tyr Arg Phe Met Gly Leu Tyr
        275                 280                 285

Glu Phe Gln Lys Ala Asp Leu Lys Asp Gly Ala Val Trp Lys Arg Val
    290                 295                 300

Lys Cys Glu Val Gln Thr Tyr Ser Pro Lys Glu Thr Lys Cys
305                 310                 315

<210> SEQ ID NO 9
<211> LENGTH: 318
<212> TYPE: PRT
<213> ORGANISM: Acinetobacter calcoaceticus

<400> SEQUENCE: 9

Met Phe Ser Ser Asp Leu Thr Asp Tyr Val Ile Arg Gln Leu Gly Arg
  1               5                  10                  15

Thr Lys Asn Lys Arg Tyr Glu Ala Tyr Val Val Ser Arg Ile Ile His
                 20                  25                  30

Leu Leu Asn Asp Phe Thr Leu Lys Phe Val Thr Gln Gln Phe Val Arg
            35                  40                  45

Leu Ser Asn Lys Lys Ile Ala Leu Thr Asp Leu Tyr Phe Pro Gln Leu
     50                  55                  60

Asp Ile His Ile Glu Val Asp Glu Gly His His Phe Leu Arg Asn Ser
 65                  70                  75                  80

Lys Met Glu Tyr Ser Leu Asn Gln Ile Asp Glu Pro Leu Tyr Ser Ile
                 85                  90                  95

Ser Gln Thr Glu Ser Asp Ala Met Arg Glu Glu Asp Ile Ile Ser Ile
```

```
            100                 105                 110
Thr Gly His Lys Ile Phe Arg Val Asn Val Tyr Lys Asn Gln Glu Gly
            115                 120                 125
Glu Pro Gln Asn Leu Glu Ser Ile His Gln Gln Ile Asp Lys Ile Ile
            130                 135                 140
Glu Glu Ile Lys Val Ala Lys Asn Lys Gln Ile Lys Ala Ser Thr Phe
145                 150                 155                 160
Lys Glu Trp Asn Ile Glu Thr Glu Tyr Asn Pro Gln Thr Tyr Ile Asp
                165                 170                 175
Leu Gly Ser Ile Ser Leu Ala Asp Asn Val Val Leu Lys Thr Thr Lys
                180                 185                 190
Asp Val Cys Asn Cys Phe Gly Tyr Asn Tyr Lys Asn Tyr Gln Arg Gly
                195                 200                 205
Gly Ala Ile His Pro Tyr Glu Lys Asp Thr Leu Ile Trp Phe Pro Arg
            210                 215                 220
Leu Tyr Glu Asn Lys Asp Trp Ile Asn Thr Ile Ser Pro Asp Gly Leu
225                 230                 235                 240
Thr Ile Thr Glu Lys Ser Thr Asp Glu Ala Ile Thr Leu Lys Lys Leu
                245                 250                 255
Glu Glu Trp Lys Asn Gly Pro Gln Lys Arg Ile Val Phe Ala Arg Val
                260                 265                 270
Lys Asp Asn Leu Ser Ser Arg Ala Met Tyr Arg Phe Met Gly Leu Tyr
                275                 280                 285
Glu Phe Gln Lys Ala Asp Leu Lys Asp Gly Ala Val Trp Lys Arg Glu
            290                 295                 300
Gly Cys Lys Val Gln Thr Tyr Ser Pro Lys Glu Ala Lys Cys
305                 310                 315

<210> SEQ ID NO 10
<211> LENGTH: 296
<212> TYPE: PRT
<213> ORGANISM: Paraprevotella xylaniphila

<400> SEQUENCE: 10

Val Lys Tyr Gly Thr Asn Ser Lys Phe Lys Asp Met Asp Tyr Lys Leu
1               5                   10                  15
Asp Tyr Met Glu Arg Leu Phe Ala Lys Ile Ser Lys Lys Lys Thr Glu
                20                  25                  30
Ser Tyr Val Ile Ser Arg Ile Trp His Gln Leu Asp Asp Asp Arg Val
                35                  40                  45
Lys Phe Val Val Gln Gln Tyr Ile Arg Arg Thr Gln Asp Lys Tyr Ala
            50                  55                  60
Leu Ala Asp Leu Tyr Leu Pro Gln Leu Asn Ile Phe Ile Glu Ile Asn
65                  70                  75                  80
Glu Pro Phe His Lys Asn Asn Thr Glu Ile Asp Lys Ile Arg Asn Glu
                85                  90                  95
Glu Ile Leu Asn Ile Thr Asn Ser Lys Pro Ile Ile Ile Asp Cys Asp
                100                 105                 110
Asn Asn Ile Gln Glu Ile His His Gln Ile Thr Asp Val Val Ser Leu
            115                 120                 125
Ile Lys Gln Cys Ile Gln Glu Met Gly Asp Asn Phe Gln Pro Trp Asp
            130                 135                 140
Asp Val Ser Thr Leu Ser Val Glu Tyr His Arg Asn Lys Gly Tyr Leu
145                 150                 155                 160
```

```
Lys Val Asp Asp Asn Glu Cys Leu Arg Thr Thr Asp Asp Val Ala Glu
            165                 170                 175

Thr Phe Gly Thr Lys Pro Lys His Arg Gly Phe Leu Arg Ala Ser Gly
        180                 185                 190

Ala Ala Val Pro Asn Lys Lys Asn Glu Ile Ile Trp Trp Pro Asn Thr
        195                 200                 205

Glu His Arg Leu Trp Cys Asn Glu Leu Ser Glu Asp Gly Met Phe Ile
    210                 215                 220

Tyr Glu Tyr Pro Lys Ala Glu Asn Lys Arg Thr Ala His Leu Lys Gln
225                 230                 235                 240

Trp Leu Ser Ala Pro Glu Glu Thr Arg Ile Thr Phe Leu Arg Tyr Lys
                245                 250                 255

Asp Asp Leu Gly Phe Cys Phe Tyr Arg Phe Val Gly Val Phe Asn Leu
            260                 265                 270

Asn Lys Glu Lys Ser Ile Lys Glu Asn Lys Cys Val Trp Glu Arg Val
        275                 280                 285

Ser Asn Thr Tyr Gln Leu Asn Val
    290                 295

<210> SEQ ID NO 11
<211> LENGTH: 321
<212> TYPE: PRT
<213> ORGANISM: Naegleria gruberi

<400> SEQUENCE: 11

Met Thr Thr Phe Lys Gln Gln Thr Ile Lys Glu Lys Glu Thr Lys Arg
1               5                   10                  15

Lys Tyr Cys Ile Lys Gly Thr Thr Ala Asn Leu Thr Gln Thr His Pro
            20                  25                  30

Asn Gly Pro Val Cys Val Asn Arg Gly Glu Glu Val Ala Asn Thr Thr
        35                  40                  45

Thr Leu Leu Asp Ser Gly Gly Gly Ile Asn Lys Lys Ser Leu Leu Gln
    50                  55                  60

Asn Leu Leu Ser Lys Cys Lys Thr Thr Phe Gln Gln Ser Phe Thr Asn
65                  70                  75                  80

Ala Asn Ile Thr Leu Lys Asp Glu Lys Trp Leu Lys Asn Val Arg Thr
                85                  90                  95

Ala Tyr Phe Val Cys Asp His Asp Gly Ser Val Glu Leu Ala Tyr Leu
            100                 105                 110

Pro Asn Val Leu Pro Lys Glu Leu Val Glu Glu Phe Thr Glu Lys Phe
        115                 120                 125

Glu Ser Ile Gln Thr Gly Arg Lys Lys Asp Thr Gly Tyr Ser Gly Ile
    130                 135                 140

Leu Asp Asn Ser Met Pro Phe Asn Tyr Val Thr Ala Asp Leu Ser Gln
145                 150                 155                 160

Glu Leu Gly Gln Tyr Leu Ser Glu Ile Val Asn Pro Gln Ile Asn Tyr
                165                 170                 175

Tyr Ile Ser Lys Leu Leu Thr Cys Val Ser Ser Arg Thr Ile Asn Tyr
            180                 185                 190

Leu Val Ser Leu Asn Asp Ser Tyr Tyr Ala Leu Asn Asn Cys Leu Tyr
        195                 200                 205

Pro Ser Thr Ala Phe Asn Ser Leu Lys Pro Ser Asn Asp Gly His Arg
    210                 215                 220

Ile Arg Lys Pro His Lys Asp Asn Leu Asp Ile Thr Pro Ser Ser Leu
225                 230                 235                 240
```

```
Phe Tyr Phe Gly Asn Phe Gln Asn Thr Glu Gly Tyr Leu Glu Leu Thr
                245                 250                 255

Asp Lys Asn Cys Lys Val Phe Val Gln Pro Gly Asp Val Leu Phe Phe
            260                 265                 270

Lys Gly Asn Glu Tyr Lys His Val Val Ala Asn Ile Thr Ser Gly Trp
        275                 280                 285

Arg Ile Gly Leu Val Tyr Phe Ala His Lys Gly Ser Lys Thr Lys Pro
    290                 295                 300

Tyr Tyr Glu Asp Thr Gln Lys Asn Ser Leu Lys Ile His Lys Glu Thr
305                 310                 315                 320

Lys

<210> SEQ ID NO 12
<211> LENGTH: 2039
<212> TYPE: PRT
<213> ORGANISM: Mus musculus

<400> SEQUENCE: 12

Met Ser Arg Ser Arg Pro Ala Lys Pro Ser Lys Ser Val Lys Thr Lys
1               5                   10                  15

Leu Gln Lys Lys Lys Asp Ile Gln Met Lys Thr Lys Thr Ser Lys Gln
                20                  25                  30

Ala Val Arg His Gly Ala Ser Ala Lys Ala Val Asn Pro Gly Lys Pro
            35                  40                  45

Lys Gln Leu Ile Lys Arg Arg Asp Gly Lys Lys Glu Thr Glu Asp Lys
        50                  55                  60

Thr Pro Thr Pro Ala Pro Ser Phe Leu Thr Arg Ala Gly Ala Ala Arg
65                  70                  75                  80

Met Asn Arg Asp Arg Asn Gln Val Leu Phe Gln Asn Pro Asp Ser Leu
                85                  90                  95

Thr Cys Asn Gly Phe Thr Met Ala Leu Arg Arg Thr Ser Leu Ser Trp
                100                 105                 110

Arg Leu Ser Gln Arg Pro Val Val Thr Pro Lys Pro Lys Lys Val Pro
            115                 120                 125

Pro Ser Lys Lys Gln Cys Thr His Asn Ile Gln Asp Glu Pro Gly Val
        130                 135                 140

Lys His Ser Glu Asn Asp Ser Val Pro Ser Gln His Ala Thr Val Ser
145                 150                 155                 160

Pro Gly Thr Glu Asn Gly Glu Gln Asn Arg Cys Leu Val Glu Gly Glu
                165                 170                 175

Ser Gln Glu Ile Thr Gln Ser Cys Pro Val Phe Glu Glu Arg Ile Glu
                180                 185                 190

Asp Thr Gln Ser Cys Ile Ser Ala Ser Gly Asn Leu Glu Ala Glu Ile
            195                 200                 205

Ser Trp Pro Leu Glu Gly Thr His Cys Glu Glu Leu Leu Ser His Gln
        210                 215                 220

Thr Ser Asp Asn Glu Cys Thr Ser Pro Gln Glu Cys Ala Pro Leu Pro
225                 230                 235                 240

Gln Arg Ser Thr Ser Glu Val Thr Ser Gln Lys Asn Thr Ser Asn Gln
                245                 250                 255

Leu Ala Asp Leu Ser Ser Gln Val Glu Ser Ile Lys Leu Ser Asp Pro
                260                 265                 270

Ser Pro Asn Pro Thr Gly Ser Asp His Asn Gly Phe Pro Asp Ser Ser
            275                 280                 285
```

```
Phe Arg Ile Val Pro Glu Leu Asp Leu Lys Thr Cys Met Pro Leu Asp
    290                 295                 300

Glu Ser Val Tyr Pro Thr Ala Leu Ile Arg Phe Ile Leu Ala Gly Ser
305                 310                 315                 320

Gln Pro Asp Val Phe Asp Thr Lys Pro Gln Glu Lys Thr Leu Ile Thr
                325                 330                 335

Thr Pro Glu Gln Val Gly Ser His Pro Asn Gln Val Leu Asp Ala Thr
                340                 345                 350

Ser Val Leu Gly Gln Ala Phe Ser Thr Leu Pro Leu Gln Trp Gly Phe
        355                 360                 365

Ser Gly Ala Asn Leu Val Gln Val Glu Ala Leu Gly Lys Gly Ser Asp
    370                 375                 380

Ser Pro Glu Asp Leu Gly Ala Ile Thr Met Leu Asn Gln Gln Glu Thr
385                 390                 395                 400

Val Ala Met Asp Met Asp Arg Asn Ala Thr Pro Asp Leu Pro Ile Phe
                405                 410                 415

Leu Pro Lys Pro Pro Asn Thr Val Ala Thr Tyr Ser Ser Pro Leu Leu
                420                 425                 430

Gly Pro Glu Pro His Ser Ser Thr Ser Cys Gly Leu Glu Val Gln Gly
            435                 440                 445

Ala Thr Pro Ile Leu Thr Leu Asp Ser Gly His Thr Pro Gln Leu Pro
        450                 455                 460

Pro Asn Pro Glu Ser Ser Ser Val Pro Leu Val Ile Ala Ala Asn Gly
465                 470                 475                 480

Thr Arg Ala Glu Lys Gln Phe Gly Thr Ser Leu Phe Pro Ala Val Pro
                485                 490                 495

Gln Gly Phe Thr Val Ala Ala Glu Asn Glu Val Gln His Ala Pro Leu
            500                 505                 510

Asp Leu Thr Gln Gly Ser Gln Ala Ala Pro Ser Lys Leu Glu Gly Glu
        515                 520                 525

Ile Ser Arg Val Ser Ile Thr Gly Ser Ala Asp Val Lys Ala Thr Ala
    530                 535                 540

Met Ser Met Pro Val Thr Gln Ala Ser Thr Ser Ser Pro Pro Cys Asn
545                 550                 555                 560

Ser Thr Pro Pro Met Val Glu Arg Arg Lys Arg Lys Ala Cys Gly Val
                565                 570                 575

Cys Glu Pro Cys Gln Gln Lys Ala Asn Cys Gly Glu Cys Thr Tyr Cys
                580                 585                 590

Lys Asn Arg Lys Asn Ser His Gln Ile Cys Lys Lys Arg Lys Cys Glu
            595                 600                 605

Val Leu Lys Lys Lys Pro Glu Ala Thr Ser Gln Ala Gln Val Thr Lys
        610                 615                 620

Glu Asn Lys Arg Pro Gln Arg Glu Lys Lys Pro Lys Val Leu Lys Thr
625                 630                 635                 640

Asp Phe Asn Asn Lys Pro Val Asn Gly Pro Lys Ser Glu Ser Met Asp
                645                 650                 655

Cys Ser Arg Arg Gly His Gly Glu Glu Glu Gln Arg Leu Asp Leu Ile
            660                 665                 670

Thr His Pro Leu Glu Asn Val Arg Lys Asn Ala Gly Gly Met Thr Gly
        675                 680                 685

Ile Glu Val Glu Lys Trp Ala Pro Asn Lys Lys Ser His Leu Ala Glu
    690                 695                 700
```

-continued

```
Gly Gln Val Lys Gly Ser Cys Asp Ala Asn Leu Thr Gly Val Glu Asn
705                 710                 715                 720

Pro Gln Pro Ser Glu Asp Lys Gln Gln Thr Asn Pro Ser Pro Thr
            725                 730                 735

Phe Ala Gln Thr Ile Arg Asn Gly Met Lys Asn Val His Cys Leu Pro
            740                 745                 750

Thr Asp Thr His Leu Pro Leu Asn Lys Leu Asn His Glu Glu Phe Ser
            755                 760                 765

Lys Ala Leu Gly Asn Asn Ser Ser Lys Leu Leu Thr Asp Pro Ser Asn
770                 775                 780

Cys Lys Asp Ala Met Ser Val Thr Thr Ser Gly Gly Glu Cys Asp His
785                 790                 795                 800

Leu Lys Gly Pro Arg Asn Thr Leu Leu Phe Gln Lys Pro Gly Leu Asn
            805                 810                 815

Cys Arg Ser Gly Ala Glu Pro Thr Ile Phe Asn Asn His Pro Asn Thr
            820                 825                 830

His Ser Ala Gly Ser Arg Pro His Pro Pro Glu Lys Val Pro Asn Lys
            835                 840                 845

Glu Pro Lys Asp Gly Ser Pro Val Gln Pro Ser Leu Leu Ser Leu Met
850                 855                 860

Lys Asp Arg Arg Leu Thr Leu Glu Gln Val Val Ala Ile Glu Ala Leu
865                 870                 875                 880

Thr Gln Leu Ser Glu Ala Pro Ser Glu Ser Ser Pro Ser Lys Pro
            885                 890                 895

Glu Lys Asp Glu Glu Ala His Gln Lys Thr Ala Ser Leu Leu Asn Ser
            900                 905                 910

Cys Lys Ala Ile Leu His Ser Val Arg Lys Asp Leu Gln Asp Pro Asn
            915                 920                 925

Val Gln Gly Lys Gly Leu His His Asp Thr Val Val Phe Asn Gly Gln
            930                 935                 940

Asn Arg Thr Phe Lys Ser Pro Asp Ser Phe Ala Thr Asn Gln Ala Leu
945                 950                 955                 960

Ile Lys Ser Gln Gly Tyr Pro Ser Ser Pro Thr Ala Glu Lys Lys Gly
            965                 970                 975

Ala Ala Gly Gly Arg Ala Pro Phe Asp Gly Phe Glu Asn Ser His Pro
            980                 985                 990

Leu Pro Ile Glu Ser His Asn Leu  Glu Asn Cys Ser Gln  Val Leu Ser
            995                 1000                1005

Cys Asp Gln Asn Leu Ser Ser  His Asp Pro Ser Cys  Gln Asp Ala
    1010                1015                1020

Pro Tyr Ser Gln Ile Glu Glu  Asp Val Ala Ala Gln  Leu Thr Gln
    1025                1030                1035

Leu Ala Ser Thr Ile Asn His  Ile Asn Ala Glu Val  Arg Asn Ala
    1040                1045                1050

Glu Ser Thr Pro Glu Ser Leu  Val Ala Lys Asn Thr  Lys Gln Lys
    1055                1060                1065

His Ser Gln Glu Lys Arg Met  Val His Gln Lys Pro  Pro Ser Ser
    1070                1075                1080

Thr Gln Thr Lys Pro Ser Val  Pro Ser Ala Lys Pro  Lys Lys Ala
    1085                1090                1095

Gln Lys Lys Ala Arg Ala Thr  Pro His Ala Asn Lys  Arg Lys Lys
    1100                1105                1110

Lys Pro Pro Ala Arg Ser Ser  Gln Glu Asn Asp Gln  Lys Lys Gln
```

-continued

```
            1115                1120                1125

Glu Gln Leu Ala Ile Glu Tyr Ser Lys Met His Asp Ile Trp Met
    1130                1135                1140

Ser Ser Lys Phe Gln Arg Phe Gly Gln Ser Ser Pro Arg Ser Phe
    1145                1150                1155

Pro Val Leu Leu Arg Asn Ile Pro Val Phe Asn Gln Ile Leu Lys
    1160                1165                1170

Pro Val Thr Gln Ser Lys Thr Pro Ser Gln His Asn Glu Leu Phe
    1175                1180                1185

Pro Pro Ile Asn Gln Ile Lys Phe Thr Arg Asn Pro Glu Leu Ala
    1190                1195                1200

Lys Glu Lys Val Lys Val Glu Pro Ser Asp Ser Leu Pro Thr Cys
    1205                1210                1215

Gln Phe Lys Thr Glu Ser Gly Gly Gln Thr Phe Ala Glu Pro Ala
    1220                1225                1230

Asp Asn Ser Gln Gly Gln Pro Met Val Ser Val Asn Gln Glu Ala
    1235                1240                1245

His Pro Leu Pro Gln Ser Pro Pro Ser Asn Gln Cys Ala Asn Ile
    1250                1255                1260

Met Ala Gly Ala Ala Gln Thr Gln Phe His Leu Gly Ala Gln Glu
    1265                1270                1275

Asn Leu Val His Gln Ile Pro Pro Pro Thr Leu Pro Gly Thr Ser
    1280                1285                1290

Pro Asp Thr Leu Leu Pro Asp Pro Ala Ser Ile Leu Arg Lys Gly
    1295                1300                1305

Lys Val Leu His Phe Asp Gly Ile Thr Val Val Thr Glu Lys Arg
    1310                1315                1320

Glu Ala Gln Thr Ser Ser Asn Gly Pro Leu Gly Pro Thr Thr Asp
    1325                1330                1335

Ser Ala Gln Ser Glu Phe Lys Glu Ser Ile Met Asp Leu Leu Ser
    1340                1345                1350

Lys Pro Ala Lys Asn Leu Ile Ala Gly Leu Lys Glu Gln Glu Ala
    1355                1360                1365

Ala Pro Cys Asp Cys Asp Gly Gly Thr Gln Lys Glu Lys Gly Pro
    1370                1375                1380

Tyr Tyr Thr His Leu Gly Ala Gly Pro Ser Val Ala Ala Val Arg
    1385                1390                1395

Glu Leu Met Glu Thr Arg Phe Gly Gln Lys Gly Lys Ala Ile Arg
    1400                1405                1410

Ile Glu Lys Ile Val Phe Thr Gly Lys Glu Gly Lys Ser Ser Gln
    1415                1420                1425

Gly Cys Pro Val Ala Lys Trp Val Ile Arg Arg Ser Gly Pro Glu
    1430                1435                1440

Glu Lys Leu Ile Cys Leu Val Arg Glu Arg Val Asp His His Cys
    1445                1450                1455

Ser Thr Ala Val Ile Val Val Leu Ile Leu Leu Trp Glu Gly Ile
    1460                1465                1470

Pro Arg Leu Met Ala Asp Arg Leu Tyr Lys Glu Leu Thr Glu Asn
    1475                1480                1485

Leu Arg Ser Tyr Ser Gly His Pro Thr Asp Arg Arg Cys Thr Leu
    1490                1495                1500

Asn Lys Lys Arg Thr Cys Thr Cys Gln Gly Ile Asp Pro Lys Thr
    1505                1510                1515
```

```
Cys Gly Ala Ser Phe Ser Phe Gly Cys Ser Trp Ser Met Tyr Phe
1520                1525                1530

Asn Gly Cys Lys Phe Gly Arg Ser Glu Asn Pro Arg Lys Phe Arg
1535                1540                1545

Leu Ala Pro Asn Tyr Pro Leu His Asn Tyr Tyr Lys Arg Ile Thr
1550                1555                1560

Gly Met Ser Ser Glu Gly Ser Asp Val Lys Thr Gly Trp Ile Ile
1565                1570                1575

Pro Asp Arg Lys Thr Leu Ile Ser Arg Glu Glu Lys Gln Leu Glu
1580                1585                1590

Lys Asn Leu Gln Glu Leu Ala Thr Val Leu Ala Pro Leu Tyr Lys
1595                1600                1605

Gln Met Ala Pro Val Ala Tyr Gln Asn Gln Val Glu Tyr Glu Glu
1610                1615                1620

Val Ala Gly Asp Cys Arg Leu Gly Asn Glu Glu Gly Arg Pro Phe
1625                1630                1635

Ser Gly Val Thr Cys Cys Met Asp Phe Cys Ala His Ser His Lys
1640                1645                1650

Asp Ile His Asn Met His Asn Gly Ser Thr Val Val Cys Thr Leu
1655                1660                1665

Ile Arg Ala Asp Gly Arg Asp Thr Asn Cys Pro Glu Asp Glu Gln
1670                1675                1680

Leu His Val Leu Pro Leu Tyr Arg Leu Ala Asp Thr Asp Glu Phe
1685                1690                1695

Gly Ser Val Glu Gly Met Lys Ala Lys Ile Lys Ser Gly Ala Ile
1700                1705                1710

Gln Val Asn Gly Pro Thr Arg Lys Arg Arg Leu Arg Phe Thr Glu
1715                1720                1725

Pro Val Pro Arg Cys Gly Lys Arg Ala Lys Met Lys Gln Asn His
1730                1735                1740

Asn Lys Ser Gly Ser His Asn Thr Lys Ser Phe Ser Ser Ala Ser
1745                1750                1755

Ser Thr Ser His Leu Val Lys Asp Glu Ser Thr Asp Phe Cys Pro
1760                1765                1770

Leu Gln Ala Ser Ser Ala Glu Thr Ser Thr Cys Thr Tyr Ser Lys
1775                1780                1785

Thr Ala Ser Gly Gly Phe Ala Glu Thr Ser Ser Ile Leu His Cys
1790                1795                1800

Thr Met Pro Ser Gly Ala His Ser Gly Ala Asn Ala Ala Ala Gly
1805                1810                1815

Glu Cys Thr Gly Thr Val Gln Pro Ala Glu Val Ala Ala His Pro
1820                1825                1830

His Gln Ser Leu Pro Thr Ala Asp Ser Pro Val His Ala Glu Pro
1835                1840                1845

Leu Thr Ser Pro Ser Glu Gln Leu Thr Ser Asn Gln Ser Asn Gln
1850                1855                1860

Gln Leu Pro Leu Leu Ser Asn Ser Gln Lys Leu Ala Ser Cys Gln
1865                1870                1875

Val Glu Asp Glu Arg His Pro Glu Ala Asp Glu Pro Gln His Pro
1880                1885                1890

Glu Asp Asp Asn Leu Pro Gln Leu Asp Glu Phe Trp Ser Asp Ser
1895                1900                1905
```

```
Glu Glu Ile Tyr Ala Asp Pro Ser Phe Gly Gly Val Ala Ile Ala
    1910                1915                1920

Pro Ile His Gly Ser Val Leu Ile Glu Cys Ala Arg Lys Glu Leu
    1925                1930                1935

His Ala Thr Thr Ser Leu Arg Ser Pro Lys Arg Gly Val Pro Phe
    1940                1945                1950

Arg Val Ser Leu Val Phe Tyr Gln His Lys Ser Leu Asn Lys Pro
    1955                1960                1965

Asn His Gly Phe Asp Ile Asn Lys Ile Lys Cys Lys Cys Lys Lys
    1970                1975                1980

Val Thr Lys Lys Lys Pro Ala Asp Arg Glu Cys Pro Asp Val Ser
    1985                1990                1995

Pro Glu Ala Asn Leu Ser His Gln Ile Pro Ser Arg Val Ala Ser
    2000                2005                2010

Thr Leu Thr Arg Asp Asn Val Val Thr Val Ser Pro Tyr Ser Leu
    2015                2020                2025

Thr His Val Ala Gly Pro Tyr Asn Arg Trp Val
    2030                2035

<210> SEQ ID NO 13
<211> LENGTH: 1912
<212> TYPE: PRT
<213> ORGANISM: Mus musculus

<400> SEQUENCE: 13

Met Glu Gln Asp Arg Thr Thr His Ala Glu Gly Thr Arg Leu Ser Pro
1               5                   10                  15

Phe Leu Ile Ala Pro Pro Ser Pro Ile Ser His Thr Glu Pro Leu Ala
                20                  25                  30

Val Lys Leu Gln Asn Gly Ser Pro Leu Ala Glu Arg Pro His Pro Glu
            35                  40                  45

Val Asn Gly Asp Thr Lys Trp Gln Ser Ser Gln Ser Cys Tyr Gly Ile
        50                  55                  60

Ser His Met Lys Gly Ser Gln Ser Ser His Glu Ser Pro His Glu Asp
65                  70                  75                  80

Arg Gly Tyr Ser Arg Cys Leu Gln Asn Gly Ile Lys Arg Thr Val
                85                  90                  95

Ser Glu Pro Ser Leu Ser Gly Leu His Pro Asn Lys Ile Leu Lys Leu
                100                 105                 110

Asp Gln Lys Ala Lys Gly Glu Ser Asn Ile Phe Glu Glu Ser Gln Glu
            115                 120                 125

Arg Asn His Gly Lys Ser Ser Arg Gln Pro Asn Val Ser Gly Leu Ser
        130                 135                 140

Asp Asn Gly Glu Pro Val Thr Ser Thr Thr Gln Glu Ser Ser Gly Ala
145                 150                 155                 160

Asp Ala Phe Pro Thr Arg Asn Tyr Asn Gly Val Glu Ile Gln Val Leu
                165                 170                 175

Asn Glu Gln Glu Gly Glu Lys Gly Arg Ser Val Thr Leu Leu Lys Asn
                180                 185                 190

Lys Ile Val Leu Met Pro Asn Gly Ala Thr Val Ser Ala His Ser Glu
            195                 200                 205

Glu Asn Thr Arg Gly Glu Leu Leu Glu Lys Thr Gln Cys Tyr Pro Asp
        210                 215                 220

Cys Val Ser Ile Ala Val Gln Ser Thr Ala Ser His Val Asn Thr Pro
225                 230                 235                 240
```

```
Ser Ser Gln Ala Ala Ile Glu Leu Ser His Glu Ile Pro Gln Pro Ser
            245                 250                 255

Leu Thr Ser Ala Gln Ile Asn Phe Ser Gln Thr Ser Ser Leu Gln Leu
            260                 265                 270

Pro Pro Glu Pro Ala Ala Met Val Thr Lys Ala Cys Asp Ala Asp Asn
            275                 280                 285

Ala Ser Lys Pro Ala Ile Val Pro Gly Thr Cys Pro Phe Gln Lys Ala
            290                 295                 300

Glu His Gln Gln Lys Ser Ala Leu Asp Ile Gly Pro Ser Arg Ala Glu
305                 310                 315                 320

Asn Lys Thr Ile Gln Gly Ser Met Glu Leu Phe Ala Glu Glu Tyr Tyr
            325                 330                 335

Pro Ser Ser Asp Arg Asn Leu Gln Ala Ser His Gly Ser Ser Glu Gln
            340                 345                 350

Tyr Ser Lys Gln Lys Glu Thr Asn Gly Ala Tyr Phe Arg Gln Ser Ser
            355                 360                 365

Lys Phe Pro Lys Asp Ser Ile Ser Pro Thr Thr Val Thr Pro Pro Ser
            370                 375                 380

Gln Ser Leu Leu Ala Pro Arg Leu Val Leu Gln Pro Pro Leu Glu Gly
385                 390                 395                 400

Lys Gly Ala Leu Asn Asp Val Ala Leu Glu Glu His His Asp Tyr Pro
            405                 410                 415

Asn Arg Ser Asn Arg Thr Leu Leu Arg Glu Gly Lys Ile Asp His Gln
            420                 425                 430

Pro Lys Thr Ser Ser Gln Ser Leu Asn Pro Ser Val His Thr Pro
            435                 440                 445

Asn Pro Pro Leu Met Leu Pro Glu Gln His Gln Asn Asp Cys Gly Ser
            450                 455                 460

Pro Ser Pro Glu Lys Ser Arg Lys Met Ser Glu Tyr Leu Met Tyr Tyr
465                 470                 475                 480

Leu Pro Asn His Gly His Ser Gly Gly Leu Gln Glu His Ser Gln Tyr
            485                 490                 495

Leu Met Gly His Arg Glu Gln Glu Ile Pro Lys Asp Ala Asn Gly Lys
            500                 505                 510

Gln Thr Gln Gly Ser Val Gln Ala Ala Pro Gly Trp Ile Glu Leu Lys
            515                 520                 525

Ala Pro Asn Leu His Glu Ala Leu His Gln Thr Lys Arg Lys Asp Ile
            530                 535                 540

Ser Leu His Ser Val Leu His Ser Gln Thr Gly Pro Val Asn Gln Met
545                 550                 555                 560

Ser Ser Lys Gln Ser Thr Gly Asn Val Asn Met Pro Gly Gly Phe Gln
            565                 570                 575

Arg Leu Pro Tyr Leu Gln Lys Thr Ala Gln Pro Glu Gln Lys Ala Gln
            580                 585                 590

Met Tyr Gln Val Gln Val Asn Gln Gly Pro Ser Pro Gly Met Gly Asp
            595                 600                 605

Gln His Leu Gln Phe Gln Lys Ala Leu Tyr Gln Glu Cys Ile Pro Arg
            610                 615                 620

Thr Asp Pro Ser Ser Glu Ala His Pro Gln Ala Pro Ser Val Pro Gln
625                 630                 635                 640

Tyr His Phe Gln Gln Arg Val Asn Pro Ser Ser Asp Lys His Leu Ser
            645                 650                 655
```

-continued

```
Gln Gln Ala Thr Glu Thr Gln Arg Leu Ser Gly Phe Leu Gln His Thr
            660                 665                 670

Pro Gln Thr Gln Ala Ser Gln Thr Pro Ala Ser Gln Asn Ser Asn Phe
            675                 680                 685

Pro Gln Ile Cys Gln Gln Gln Gln Gln Leu Gln Arg Lys Asn
            690                 695                 700

Lys Glu Gln Met Pro Gln Thr Phe Ser His Leu Gln Gly Ser Asn Asp
705                 710                 715                 720

Lys Gln Arg Glu Gly Ser Cys Phe Gly Gln Ile Lys Val Glu Glu Ser
                725                 730                 735

Phe Cys Val Gly Asn Gln Tyr Ser Lys Ser Ser Asn Phe Gln Thr His
            740                 745                 750

Asn Asn Thr Gln Gly Gly Leu Glu Gln Val Gln Asn Ile Asn Lys Asn
            755                 760                 765

Phe Pro Tyr Ser Lys Ile Leu Thr Pro Asn Ser Ser Asn Leu Gln Ile
            770                 775                 780

Leu Pro Ser Asn Asp Thr His Pro Ala Cys Glu Arg Glu Gln Ala Leu
785                 790                 795                 800

His Pro Val Gly Ser Lys Thr Ser Asn Leu Gln Asn Met Gln Tyr Phe
                805                 810                 815

Pro Asn Asn Val Thr Pro Asn Gln Asp Val His Arg Cys Phe Gln Glu
            820                 825                 830

Gln Ala Gln Lys Pro Gln Gln Ala Ser Ser Leu Gln Gly Leu Lys Asp
            835                 840                 845

Arg Ser Gln Gly Glu Ser Pro Ala Pro Pro Ala Glu Ala Ala Gln Gln
850                 855                 860

Arg Tyr Leu Val His Asn Glu Ala Lys Ala Leu Pro Val Pro Glu Gln
865                 870                 875                 880

Gly Gly Ser Gln Thr Gln Thr Pro Pro Gln Lys Asp Thr Gln Lys His
                885                 890                 895

Ala Ala Leu Arg Trp Leu Leu Leu Gln Lys Gln Glu Gln Gln Gln Thr
            900                 905                 910

Gln Gln Ser Gln Pro Gly His Asn Gln Met Leu Arg Pro Ile Lys Thr
            915                 920                 925

Glu Pro Val Ser Lys Pro Ser Ser Tyr Arg Tyr Pro Leu Ser Pro Pro
            930                 935                 940

Gln Glu Asn Met Ser Ser Arg Ile Lys Gln Glu Ile Ser Ser Pro Ser
945                 950                 955                 960

Arg Asp Asn Gly Gln Pro Lys Ser Ile Ile Glu Thr Met Glu Gln His
                965                 970                 975

Leu Lys Gln Phe Gln Leu Lys Ser Leu Cys Asp Tyr Lys Ala Leu Thr
            980                 985                 990

Leu Lys Ser Gln Lys His Val Lys  Val Pro Thr Asp Ile  Gln Ala Ala
            995                 1000                1005

Glu Ser  Glu Asn His Ala Arg  Ala Ala Glu Pro Gln  Ala Thr Lys
    1010                1015                 1020

Ser Thr  Asp Cys Ser Val Leu  Asp Asp Val Ser Glu  Ser Asp Thr
    1025                1030                 1035

Pro Gly  Glu Gln Ser Gln Asn  Gly Lys Cys Glu Gly  Cys Asn Pro
    1040                1045                 1050

Asp Lys  Asp Glu Ala Pro Tyr  Tyr Thr His Leu Gly  Ala Gly Pro
    1055                1060                 1065

Asp Val  Ala Ala Ile Arg Thr  Leu Met Glu Glu Arg  Tyr Gly Glu
```

-continued

```
            1070                1075                1080
Lys Gly Lys Ala Ile Arg Ile Glu Lys Val Ile Tyr Thr Gly Lys
            1085                1090                1095
Glu Gly Lys Ser Ser Gln Gly Cys Pro Ile Ala Lys Trp Val Tyr
            1100                1105                1110
Arg Arg Ser Ser Glu Glu Glu Lys Leu Leu Cys Leu Val Arg Val
            1115                1120                1125
Arg Pro Asn His Thr Cys Glu Thr Ala Val Met Val Ile Ala Ile
            1130                1135                1140
Met Leu Trp Asp Gly Ile Pro Lys Leu Leu Ala Ser Glu Leu Tyr
            1145                1150                1155
Ser Glu Leu Thr Asp Ile Leu Gly Lys Cys Gly Ile Cys Thr Asn
            1160                1165                1170
Arg Arg Cys Ser Gln Asn Glu Thr Arg Asn Cys Cys Cys Gln Gly
            1175                1180                1185
Glu Asn Pro Glu Thr Cys Gly Ala Ser Phe Ser Phe Gly Cys Ser
            1190                1195                1200
Trp Ser Met Tyr Tyr Asn Gly Cys Lys Phe Ala Arg Ser Lys Lys
            1205                1210                1215
Pro Arg Lys Phe Arg Leu His Gly Ala Glu Pro Lys Glu Glu Glu
            1220                1225                1230
Arg Leu Gly Ser His Leu Gln Asn Leu Ala Thr Val Ile Ala Pro
            1235                1240                1245
Ile Tyr Lys Lys Leu Ala Pro Asp Ala Tyr Asn Asn Gln Val Glu
            1250                1255                1260
Phe Glu His Gln Ala Pro Asp Cys Cys Leu Gly Leu Lys Glu Gly
            1265                1270                1275
Arg Pro Phe Ser Gly Val Thr Ala Cys Leu Asp Phe Ser Ala His
            1280                1285                1290
Ser His Arg Asp Gln Gln Asn Met Pro Asn Gly Ser Thr Val Val
            1295                1300                1305
Val Thr Leu Asn Arg Glu Asp Asn Arg Glu Val Gly Ala Lys Pro
            1310                1315                1320
Glu Asp Glu Gln Phe His Val Leu Pro Met Tyr Ile Ile Ala Pro
            1325                1330                1335
Glu Asp Glu Phe Gly Ser Thr Glu Gly Gln Glu Lys Lys Ile Arg
            1340                1345                1350
Met Gly Ser Ile Glu Val Leu Gln Ser Phe Arg Arg Arg Arg Val
            1355                1360                1365
Ile Arg Ile Gly Glu Leu Pro Lys Ser Cys Lys Lys Ala Glu
            1370                1375                1380
Pro Lys Lys Ala Lys Thr Lys Lys Ala Ala Arg Lys Arg Ser Ser
            1385                1390                1395
Leu Glu Asn Cys Ser Ser Arg Thr Glu Lys Gly Lys Ser Ser Ser
            1400                1405                1410
His Thr Lys Leu Met Glu Asn Ala Ser His Met Lys Gln Met Thr
            1415                1420                1425
Ala Gln Pro Gln Leu Ser Gly Pro Val Ile Arg Gln Pro Pro Thr
            1430                1435                1440
Leu Gln Arg His Leu Gln Gln Gly Gln Arg Pro Gln Gln Pro Gln
            1445                1450                1455
Pro Pro Gln Pro Gln Pro Gln Thr Thr Pro Gln Pro Gln Pro Gln
            1460                1465                1470
```

-continued

Pro Gln His Ile Met Pro Gly Asn Ser Gln Ser Val Gly Ser His
    1475            1480                1485

Cys Ser Gly Ser Thr Ser Val Tyr Thr Arg Gln Pro Thr Pro His
    1490            1495                1500

Ser Pro Tyr Pro Ser Ser Ala His Thr Ser Asp Ile Tyr Gly Asp
    1505            1510                1515

Thr Asn His Val Asn Phe Tyr Pro Thr Ser Ser His Ala Ser Gly
    1520            1525                1530

Ser Tyr Leu Asn Pro Ser Asn Tyr Met Asn Pro Tyr Leu Gly Leu
    1535            1540                1545

Leu Asn Gln Asn Asn Gln Tyr Ala Pro Phe Pro Tyr Asn Gly Ser
    1550            1555                1560

Val Pro Val Asp Asn Gly Ser Pro Phe Leu Gly Ser Tyr Ser Pro
    1565            1570                1575

Gln Ala Gln Ser Arg Asp Leu His Arg Tyr Pro Asn Gln Asp His
    1580            1585                1590

Leu Thr Asn Gln Asn Leu Pro Pro Ile His Thr Leu His Gln Gln
    1595            1600                1605

Thr Phe Gly Asp Ser Pro Ser Lys Tyr Leu Ser Tyr Gly Asn Gln
    1610            1615                1620

Asn Met Gln Arg Asp Ala Phe Thr Thr Asn Ser Thr Leu Lys Pro
    1625            1630                1635

Asn Val His His Leu Ala Thr Phe Ser Pro Tyr Pro Thr Pro Lys
    1640            1645                1650

Met Asp Ser His Phe Met Gly Ala Ala Ser Arg Ser Pro Tyr Ser
    1655            1660                1665

His Pro His Thr Asp Tyr Lys Thr Ser Glu His His Leu Pro Ser
    1670            1675                1680

His Thr Ile Tyr Ser Tyr Thr Ala Ala Ala Ser Gly Ser Ser Ser
    1685            1690                1695

Ser His Ala Phe His Asn Lys Glu Asn Asp Asn Ile Ala Asn Gly
    1700            1705                1710

Leu Ser Arg Val Leu Pro Gly Phe Asn His Asp Arg Thr Ala Ser
    1715            1720                1725

Ala Gln Glu Leu Leu Tyr Ser Leu Thr Gly Ser Ser Gln Glu Lys
    1730            1735                1740

Gln Pro Glu Val Ser Gly Gln Asp Ala Ala Ala Val Gln Glu Ile
    1745            1750                1755

Glu Tyr Trp Ser Asp Ser Glu His Asn Phe Gln Asp Pro Cys Ile
    1760            1765                1770

Gly Gly Val Ala Ile Ala Pro Thr His Gly Ser Ile Leu Ile Glu
    1775            1780                1785

Cys Ala Lys Cys Glu Val His Ala Thr Thr Lys Val Asn Asp Pro
    1790            1795                1800

Asp Arg Asn His Pro Thr Arg Ile Ser Leu Val Leu Tyr Arg His
    1805            1810                1815

Lys Asn Leu Phe Leu Pro Lys His Cys Leu Ala Leu Trp Glu Ala
    1820            1825                1830

Lys Met Ala Glu Lys Ala Arg Lys Glu Glu Glu Cys Gly Lys Asn
    1835            1840                1845

Gly Ser Asp His Val Ser Gln Lys Asn His Gly Lys Gln Glu Lys
    1850            1855                1860

```
Arg Glu Pro Thr Gly Pro Gln Glu Pro Ser Tyr Leu Arg Phe Ile
    1865                1870                1875

Gln Ser Leu Ala Glu Asn Thr Gly Ser Val Thr Thr Asp Ser Thr
    1880                1885                1890

Val Thr Thr Ser Pro Tyr Ala Phe Thr Gln Val Thr Gly Pro Tyr
    1895                1900                1905

Asn Thr Phe Val
    1910

<210> SEQ ID NO 14
<211> LENGTH: 1713
<212> TYPE: PRT
<213> ORGANISM: Mus musculus

<400> SEQUENCE: 14

Met Phe Leu Pro Glu Thr Pro Gln Gln Tyr Ala Val Glu Ile Asn Ala
1               5                   10                  15

Arg Glu Gly Thr Gly Pro Trp Ala Gln Gly Ala Thr Val Lys Thr Gly
            20                  25                  30

Ser Glu Leu Ser Pro Val Asp Gly Val Pro Gly Gln Met Asp Ser
        35                  40                  45

Gly Pro Val Tyr His Gly Asp Ser Arg Gln Leu Ser Thr Ser Gly Ala
    50                  55                  60

Pro Val Asn Gly Ala Arg Glu Pro Ala Gly Pro Gly Leu Leu Gly Ala
65                  70                  75                  80

Ala Gly Pro Trp Arg Val Asp Gln Lys Pro Asp Trp Glu Ala Ala Ser
                85                  90                  95

Gly Pro Thr His Ala Ala Arg Leu Glu Asp Ala His Asp Leu Val Ala
            100                 105                 110

Phe Ser Ala Val Ala Glu Ala Val Ser Ser Tyr Gly Ala Leu Ser Thr
        115                 120                 125

Arg Leu Tyr Glu Thr Phe Asn Arg Glu Met Ser Arg Glu Ala Gly Ser
    130                 135                 140

Asn Gly Arg Gly Pro Arg Pro Glu Ser Cys Ser Glu Gly Ser Glu Asp
145                 150                 155                 160

Leu Asp Thr Leu Gln Thr Ala Leu Ala Leu Ala Arg His Gly Met Lys
                165                 170                 175

Pro Pro Asn Cys Thr Cys Asp Gly Pro Glu Cys Pro Asp Phe Leu Glu
            180                 185                 190

Trp Leu Glu Gly Lys Ile Lys Ser Met Ala Met Glu Gly Gly Gln Gly
        195                 200                 205

Arg Pro Arg Leu Pro Gly Ala Leu Pro Pro Ser Glu Ala Gly Leu Pro
    210                 215                 220

Ala Pro Ser Thr Arg Pro Leu Leu Ser Glu Val Pro Gln Val
225                 230                 235                 240

Pro Pro Leu Glu Gly Leu Pro Leu Ser Gln Ser Ala Leu Ser Ile Ala
                245                 250                 255

Lys Glu Lys Asn Ile Ser Leu Gln Thr Ala Ile Ala Ile Glu Ala Leu
            260                 265                 270

Thr Gln Leu Ser Ser Ala Leu Pro Gln Pro Ser His Ser Thr Ser Gln
        275                 280                 285

Ala Ser Cys Pro Leu Pro Glu Ala Leu Ser Pro Ser Ala Pro Phe Arg
    290                 295                 300

Ser Pro Gln Ser Tyr Leu Arg Ala Pro Ser Trp Pro Val Val Pro Pro
305                 310                 315                 320
```

```
Glu Glu His Pro Ser Phe Ala Pro Asp Ser Pro Ala Phe Pro Pro Ala
            325                 330                 335

Thr Pro Arg Pro Glu Phe Ser Glu Ala Trp Gly Asp Thr Pro Pro
        340                 345                 350

Ala Thr Pro Arg Asn Ser Trp Pro Val Pro Arg Pro Ser Pro Asp Pro
            355                 360                 365

Met Ala Glu Leu Glu Gln Leu Leu Gly Ser Ala Ser Asp Tyr Ile Gln
    370                 375                 380

Ser Val Phe Lys Arg Pro Glu Ala Leu Pro Thr Lys Pro Lys Val Lys
385                 390                 395                 400

Val Glu Ala Pro Ser Ser Pro Ala Pro Val Pro Ser Pro Ile Ser
                405                 410                 415

Gln Arg Glu Ala Pro Leu Leu Ser Ser Glu Pro Asp Thr His Gln Lys
            420                 425                 430

Ala Gln Thr Ala Leu Gln Gln His Leu His His Lys Arg Asn Leu Phe
            435                 440                 445

Leu Glu Gln Ala Gln Asp Ala Ser Phe Pro Thr Ser Thr Glu Pro Gln
    450                 455                 460

Ala Pro Gly Trp Trp Ala Pro Gly Ser Pro Ala Pro Arg Pro Pro
465                 470                 475                 480

Asp Lys Pro Pro Lys Glu Lys Lys Lys Pro Pro Thr Pro Ala Gly
            485                 490                 495

Gly Pro Val Gly Ala Glu Lys Thr Thr Pro Gly Ile Lys Thr Ser Val
            500                 505                 510

Arg Lys Pro Ile Gln Ile Lys Lys Ser Arg Ser Arg Asp Met Gln Pro
            515                 520                 525

Leu Phe Leu Pro Val Arg Gln Ile Val Leu Glu Gly Leu Lys Pro Gln
    530                 535                 540

Ala Ser Glu Gly Gln Ala Pro Leu Pro Ala Gln Leu Ser Val Pro Pro
545                 550                 555                 560

Pro Ala Ser Gln Gly Ala Ala Ser Gln Ser Cys Ala Thr Pro Leu Thr
            565                 570                 575

Pro Glu Pro Ser Leu Ala Leu Phe Ala Pro Ser Pro Ser Gly Asp Ser
            580                 585                 590

Leu Leu Pro Pro Thr Gln Glu Met Arg Ser Pro Ser Pro Met Val Ala
            595                 600                 605

Leu Gln Ser Gly Ser Thr Gly Gly Pro Leu Pro Pro Ala Asp Asp Lys
    610                 615                 620

Leu Glu Glu Leu Ile Arg Gln Phe Glu Ala Glu Phe Gly Asp Ser Phe
625                 630                 635                 640

Gly Leu Pro Gly Pro Pro Ser Val Pro Ile Gln Glu Pro Glu Asn Gln
            645                 650                 655

Ser Thr Cys Leu Pro Ala Pro Glu Ser Pro Phe Ala Thr Arg Ser Pro
            660                 665                 670

Lys Lys Ile Lys Ile Glu Ser Ser Gly Ala Val Thr Val Leu Ser Thr
        675                 680                 685

Thr Cys Phe His Ser Glu Glu Gly Gly Gln Glu Ala Thr Pro Thr Lys
    690                 695                 700

Ala Glu Asn Pro Leu Thr Pro Thr Leu Ser Gly Phe Leu Glu Ser Pro
705                 710                 715                 720

Leu Lys Tyr Leu Asp Thr Pro Thr Lys Ser Leu Leu Asp Thr Pro Ala
            725                 730                 735
```

```
Lys Lys Ala Gln Ser Glu Phe Pro Thr Cys Asp Cys Val Glu Gln Ile
                740                 745                 750

Val Glu Lys Asp Glu Gly Pro Tyr Tyr Thr His Leu Gly Ser Gly Pro
            755                 760                 765

Thr Val Ala Ser Ile Arg Glu Leu Met Glu Asp Arg Tyr Gly Glu Lys
        770                 775                 780

Gly Lys Ala Ile Arg Ile Glu Lys Val Ile Tyr Thr Gly Lys Glu Gly
785                 790                 795                 800

Lys Ser Ser Arg Gly Cys Pro Ile Ala Lys Trp Val Ile Arg Arg His
                805                 810                 815

Thr Leu Glu Glu Lys Leu Leu Cys Leu Val Arg His Arg Ala Gly His
            820                 825                 830

His Cys Gln Asn Ala Val Ile Val Ile Leu Ile Leu Ala Trp Glu Gly
        835                 840                 845

Ile Pro Arg Ser Leu Gly Asp Thr Leu Tyr Gln Glu Leu Thr Asp Thr
    850                 855                 860

Leu Arg Lys Tyr Gly Asn Pro Thr Ser Arg Arg Cys Gly Leu Asn Asp
865                 870                 875                 880

Asp Arg Thr Cys Ala Cys Gln Gly Lys Asp Pro Asn Thr Cys Gly Ala
                885                 890                 895

Ser Phe Ser Phe Gly Cys Ser Trp Ser Met Tyr Phe Asn Gly Cys Lys
            900                 905                 910

Tyr Ala Arg Ser Lys Thr Pro Arg Lys Phe Arg Leu Thr Gly Asp Asn
        915                 920                 925

Pro Lys Glu Glu Glu Val Leu Arg Asn Ser Phe Gln Asp Leu Ala Thr
    930                 935                 940

Glu Val Ala Pro Leu Tyr Lys Arg Leu Ala Pro Gln Ala Tyr Gln Asn
945                 950                 955                 960

Gln Val Thr Asn Glu Asp Val Ala Ile Asp Cys Arg Leu Gly Leu Lys
                965                 970                 975

Glu Gly Arg Pro Phe Ser Gly Val Thr Ala Cys Met Asp Phe Cys Ala
            980                 985                 990

His Ala His Lys Asp Gln His Asn Leu Tyr Asn Gly Cys Thr Val Val
        995                 1000                1005

Cys Thr Leu Thr Lys Glu Asp Asn Arg Cys Val Gly Gln Ile Pro
    1010                1015                1020

Glu Asp Glu Gln Leu His Val Leu Pro Leu Tyr Lys Met Ala Ser
    1025                1030                1035

Thr Asp Glu Phe Gly Ser Glu Asn Gln Asn Ala Lys Val Ser
    1040                1045                1050

Ser Gly Ala Ile Gln Val Leu Thr Ala Phe Pro Arg Glu Val Arg
    1055                1060                1065

Arg Leu Pro Glu Pro Ala Lys Ser Cys Arg Gln Arg Gln Leu Glu
    1070                1075                1080

Ala Arg Lys Ala Ala Glu Lys Lys Lys Leu Gln Lys Glu Lys
    1085                1090                1095

Leu Ser Thr Pro Glu Lys Ile Lys Gln Glu Ala Leu Glu Leu Ala
    1100                1105                1110

Gly Val Thr Thr Asp Pro Gly Leu Ser Leu Lys Gly Gly Leu Ser
    1115                1120                1125

Gln Gln Ser Leu Lys Pro Ser Leu Lys Val Glu Pro Gln Asn His
    1130                1135                1140

Phe Ser Ser Phe Lys Tyr Ser Gly Asn Ala Val Val Glu Ser Tyr
```

```
              1145                1150                1155
Ser  Val  Leu  Gly  Ser  Cys  Arg  Pro  Ser  Asp  Pro  Tyr  Ser  Met  Ser
              1160                1165                1170
Ser  Val  Tyr  Ser  Tyr  His  Ser  Arg  Tyr  Ala  Gln  Pro  Gly  Leu  Ala
              1175                1180                1185
Ser  Val  Asn  Gly  Phe  His  Ser  Lys  Tyr  Thr  Leu  Pro  Ser  Phe  Gly
              1190                1195                1200
Tyr  Tyr  Gly  Phe  Pro  Ser  Ser  Asn  Pro  Val  Phe  Pro  Ser  Gln  Phe
              1205                1210                1215
Leu  Gly  Pro  Ser  Ala  Trp  Gly  His  Gly  Gly  Ser  Gly  Gly  Ser  Phe
              1220                1225                1230
Glu  Lys  Lys  Pro  Asp  Leu  His  Ala  Leu  His  Asn  Ser  Leu  Asn  Pro
              1235                1240                1245
Ala  Tyr  Gly  Gly  Ala  Glu  Phe  Ala  Glu  Leu  Pro  Gly  Gln  Ala  Val
              1250                1255                1260
Ala  Thr  Asp  Asn  His  His  Pro  Ile  Pro  His  His  Gln  Gln  Pro  Ala
              1265                1270                1275
Tyr  Pro  Gly  Pro  Lys  Glu  Tyr  Leu  Leu  Pro  Lys  Val  Pro  Gln  Leu
              1280                1285                1290
His  Pro  Ala  Ser  Arg  Asp  Pro  Ser  Pro  Phe  Ala  Gln  Ser  Ser  Ser
              1295                1300                1305
Cys  Tyr  Asn  Arg  Ser  Ile  Lys  Gln  Glu  Pro  Ile  Asp  Pro  Leu  Thr
              1310                1315                1320
Gln  Ala  Glu  Ser  Ile  Pro  Arg  Asp  Ser  Ala  Lys  Met  Ser  Arg  Thr
              1325                1330                1335
Pro  Leu  Pro  Glu  Ala  Ser  Gln  Asn  Gly  Gly  Pro  Ser  His  Leu  Trp
              1340                1345                1350
Gly  Gln  Tyr  Ser  Gly  Gly  Pro  Ser  Met  Ser  Pro  Lys  Arg  Thr  Asn
              1355                1360                1365
Ser  Val  Gly  Gly  Asn  Trp  Gly  Val  Phe  Pro  Pro  Gly  Glu  Ser  Pro
              1370                1375                1380
Thr  Ile  Val  Pro  Asp  Lys  Leu  Asn  Ser  Phe  Gly  Ala  Ser  Cys  Leu
              1385                1390                1395
Thr  Pro  Ser  His  Phe  Pro  Glu  Ser  Gln  Trp  Gly  Leu  Phe  Thr  Gly
              1400                1405                1410
Glu  Gly  Gln  Gln  Ser  Ala  Pro  His  Ala  Gly  Ala  Arg  Leu  Arg  Gly
              1415                1420                1425
Lys  Pro  Trp  Ser  Pro  Cys  Lys  Phe  Gly  Asn  Gly  Thr  Ser  Ala  Leu
              1430                1435                1440
Thr  Gly  Pro  Ser  Leu  Thr  Glu  Lys  Pro  Trp  Gly  Met  Gly  Thr  Gly
              1445                1450                1455
Asp  Phe  Asn  Pro  Ala  Leu  Lys  Gly  Gly  Pro  Gly  Phe  Gln  Asp  Lys
              1460                1465                1470
Leu  Trp  Asn  Pro  Val  Lys  Val  Glu  Glu  Gly  Arg  Ile  Pro  Thr  Pro
              1475                1480                1485
Gly  Ala  Asn  Pro  Leu  Asp  Lys  Ala  Trp  Gln  Ala  Phe  Gly  Met  Pro
              1490                1495                1500
Leu  Ser  Ser  Asn  Glu  Lys  Leu  Phe  Gly  Ala  Leu  Lys  Ser  Glu  Glu
              1505                1510                1515
Lys  Leu  Trp  Asp  Pro  Phe  Ser  Leu  Glu  Glu  Gly  Thr  Ala  Glu  Glu
              1520                1525                1530
Pro  Pro  Ser  Lys  Gly  Val  Val  Lys  Glu  Glu  Lys  Ser  Gly  Pro  Thr
              1535                1540                1545
```

-continued

```
Val Glu Glu Asp Glu Glu Glu Leu Trp Ser Asp Ser Glu His Asn
    1550                1555            1560
Phe Leu Asp Glu Asn Ile Gly Gly Val Ala Val Ala Pro Ala His
    1565                1570            1575
Cys Ser Ile Leu Ile Glu Cys Ala Arg Arg Glu Leu His Ala Thr
    1580                1585            1590
Thr Pro Leu Lys Lys Pro Asn Arg Cys His Pro Thr Arg Ile Ser
    1595                1600            1605
Leu Val Phe Tyr Gln His Lys Asn Leu Asn Gln Pro Asn His Gly
    1610                1615            1620
Leu Ala Leu Trp Glu Ala Lys Met Lys Gln Leu Ala Glu Arg Ala
    1625                1630            1635
Arg Gln Arg Gln Glu Glu Ala Ala Arg Leu Gly Leu Gly Gln Gln
    1640                1645            1650
Glu Ala Lys Leu Tyr Gly Lys Lys Arg Lys Trp Gly Gly Ala Met
    1655                1660            1665
Val Ala Glu Pro Gln His Lys Glu Lys Lys Gly Ala Ile Pro Thr
    1670                1675            1680
Arg Gln Ala Leu Ala Met Pro Thr Asp Ser Ala Val Thr Val Ser
    1685                1690            1695
Ser Tyr Ala Tyr Thr Lys Val Thr Gly Pro Tyr Ser Arg Trp Ile
    1700                1705            1710
```

MAPPING CYTOSINE MODIFICATIONS

CROSS REFERENCE

This application is a continuation-in-part of U.S. application Ser. No. 13/826,395 filed Mar. 14, 2013.

GOVERNMENT RIGHTS

This invention was made with government support under GM096723 awarded by the National Institutes of Health. The government has certain rights in this invention.

BACKGROUND 5-hydroxymethylcytosine (5-hmC), 5-formylcytosine (5-fC), and 5-carboxycytosine (5-caC) were recently identified in mammalian brain and embryonic stem cells as products of the oxidation of 5-methylcytosine (5-mC) by cytosine oxygenases. The biological functions of 5-hmC, 5-fC, and 5-caC are not completely understood; however, several lines of evidence suggest that 5-hmC is involved in epigenetic regulation and DNA demethylation. Iterative oxidation of 5-hmC by cytosine oxygenase enzymes yields 5-fC and 5-caC which are hypothesized to be intermediates in the DNA demethylation process. Several challenges are associated with the identification these biologically modified nucleobases in genomic DNA samples due to their low abundance and temporal fluctuation. Mapping and quantifying 5-mC, 5-hmC, 5-fC, and 5-caC at the DNA level is, therefore, important for unraveling their role in the dynamics of gene expression and regulation.

SUMMARY OF THE INVENTION

The present invention provides a variety of reagents, kits and methods for selectively altering and identifying modified nucleotides in a nucleic acid such as DNA. The modified nucleotides that can be identified include, for example, 5-mC, 5-hmC, 5-fC and 5-caC. The methods, reagents and kits of the present invention permit not merely the determination that a modified cytosine residue is present, but also permit the discrimination among or between different types of modified nucleotides, such as 5-mC and 5-hmC, or between 5-hmC and 5-fC. In this way, the invention can be used to elucidate the precise state of a modified nucleic acid, which may be a genome or genome fragment, for example.

In some embodiments, the discrimination among or between different oxidation states of a nucleotide is facilitated by alternately glucosylating or glucosaminylating various modified nucleotides. The glucosylated or glucosaminylated forms can be distinguished based on their performance in various assays, such as by their differential sensitivity to certain restriction endonucleases. In this way, alternately reacting the nucleic acid with a UDP-GlcN (Uridine diphosphate glucosamine or UDP-Glucosamine) substrate and a UDP-Glc (Uridine diphosphate glucose or UDP-Glucose) substrate, places off and on switches for endonuclease cleavage of a nucleic acid containing modified nucleotides. By detecting the presence of cleavage-sensitive sites, the modified nucleotides can be located and identified.

In the present invention, the term glucosylation (and any form of glucosylation such as "glucosylating" or "glucosylated") refers to the incorporation of a glucosyl moiety from UDP-Glc into the 5-hydroxy position of 5-hmC via the action of a glycosyltransferase to produce 5-gmC (5-glucosyloxymethylcytosine). Other names in common use for 5-gmC include glucosyl-5-hydroxymethyl-cytosine, glucosyl-5-hydroxymethylcytosine, glucosyl-oxy-5-methylcytosine, 5-glucosylhydroxymethylcytosine. In the present invention, the term glucosylation (and any form of glucosylation such as "glucosylating" or "glucosylated") may also refer to the incorporation of an azido modified glucosyl moiety from UDP-Azido-Glc (for example, UDP-6-Azido-Glc or UDP-6-N3-Glc) into the 5-hydroxy position of 5-hmC via the action of a glycosyltransferase to produce a N3-5-gmC (for example, 6-azide-glucosyl-5-hydroxymethylcytosine or 6-N3gmC). In the present invention, the term glucosaminylation (and any form of glucosaminylation such as "glucosaminylating" or "glucosaminylated") refers to the incorporation of a glucosaminyl moiety from UDP-GlcN into the 5-hydroxy position of 5-hmC via the action of a glycosyltransferase to produce 5-gNmC (5-glucosaminyloxymethylcytosine). Other names for 5-gNmC include glucosaminyl-5-hydroxymethyl-cytosine, glucosaminyl-5-hydroxymethylcytosine, 5-glucosylhydroxymethylcytosine, aminoglucosyl-5-hydroxymethyl-cytosine, aminoglucosyl-5-hydroxymethylcytosine, and 5-aminoglucosylhydroxymethylcytosine. If the glycosyltransferase is an inverting glycosyltransferase such as T4 β-glucosyltransferase (BGT or βGT or beta-GT) the product is formed with a beta glycosydic linkage (for example, 5-β-gmC, 5-β-6-N3gmC, 5-β-6-gNmC, and 5-β-2-gNmC). If the glycosyltransferase is a retaining glycosyltransferase such as T4 α-glucosyltransferase (AGT or aGT or alpha-GT) the product is formed with an alpha glycosydic linkage (for example, 5-α-gmC).

Specifically, for example, the invention permits the differentiation of 5-β-glucosyloxymethylcytosine (5-β-gmC) from 5-β-2-glucosaminyloxymethylcytosine (5-β-2-gNmC) in a nucleic acid, by reacting the nucleic acid with an endonuclease capable of cleaving a nucleic acid at a glucosylated nucleotide but not at an glucosaminylated nucleotide. One suitable endonuclease is AbaSI. Other useful endonucleases include AbaAI, AbaCI, AbaDI, AbaTI, AbaUI, AcaPI, and PxyI, or one of the ZZYZ proteins or its variants described in US Patent Application Publication No. 2012/0301881, the complete disclosure of which is hereby incorporated by reference. Accordingly, one of these endonucleases, or a polypeptide at least 70% (e.g. at least 75%, at least 80%, at least 82%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to one of those endonucleases or an active fragment thereof) can be used to selectively cleave a target nucleic acid. By controlling the conversion of glucosylation and glucosaminylation of various forms of naturally occurring modified nucleotides, the modified nucleotides can be located and identified in a manner distinguishing their original forms, such as methylcytosine, hydroxymethylcytosine, formylcytosine, and/or carboxycytosine.

Accordingly, in one aspect the invention provides methods for selectively altering modified nucleotides in a nucleic acid containing hydroxymethylated nucleotides and other modified nucleotides such as, 5-fC or 5-caC. The methods generally include reacting a first subset of the modified nucleotides (e.g. 5-hmC) in the nucleic acid with UDP-GlcN in the presence of a β-glycosyltransferase, such as T4-β-glucosyltransferase, to convert hydroxymethylated nucleotides in the nucleic acid to glucosaminylated nucleotides.

In some embodiments, the methods include the subsequent step of reacting the nucleic acid with a reducing agent, such as $NaBH_4$, and a UDP derivative, such as UDP-Glc or UDP-azido-glucose, to convert a second subset of nucleotides in the nucleic acid to glucosylated or azido-glucosylated nucleotides. The reducing agent promotes the reduction of a nucleotide in a higher oxidation state, such as 5-fC or 5-caC, to a hydroxymethylated nucleotide, which is then glucosylated or azido-glucosylated in a reaction typically catalyzed by a glycosyltransferase such as an α-glycosyltransferase or a β-glycosyltransferase. The glycosyltransferase may or may not be the same glycosyltransferase used to catalyze the previous conversion of hydroxymethylated nucleotides to glucosaminylated nucleotides. The method can optionally differentiate pre-existing 5-hmC in a nucleic acid from newly formed as a result of the reduction of 5-fC or 5-caC, for example. When a UDP-azido-glucose such as UDP-6-azido-glucose is used, 5-hmC in the nucleic acid can be converted to a β-6-azide-glucosyl-5-hydroxymethylcytosine in the presence of a β-glycosyltransferase; Further derivatization of the azido moiety via azide-alkyne Huisgen cycloaddition using a copper(I) catalyst ("click chemistry") or via copper-free variants (for example, using strained cyclooctyne derivatives) can then optionally be used to label the nucleotide, such as with a biotin label, permitting the subsequent use of avidin to selectively isolate the labeled nucleotide.

In other embodiments, following the conversion of hydroxymethylated nucleotides in the nucleic acid to glucosaminylated nucleotides, the nucleic acid is reacted with an oxidizing agent, a UDP-Glc derivative, and a glycosyltransferase to convert a second subset of modified nucleotides in the nucleic acid to glucosylated nucleotides. Suitable oxidizing agents include those capable of oxidizing 5-mC to 5-hmC, such as mYOX1, a TET enzyme, or an inorganic oxidizing agent such as $KRuO_4$. The reaction with UDP-Glc is typically conducted in the presence of a glycosyltransferase such as an α-glycosyltransferase or a β-glycosyltransferase. These methods can, for example, differentiate pre-existing 5-hmC in a nucleic acid from 5-hmC generated from a 5-mC precursor.

In any of these methods, whether incorporating a reducing agent or an oxidizing agent, an endonuclease can be used to characterize the reaction products. Typically, the endonuclease is specific for the glucosylated (or azidoglucosylated) nucleotides, and not for glucosaminylated nucleotides, i.e., the endonuclease has a higher enzymatic activity for a glucosylated or azidoglucosylated nucleic acid that it has for the same nucleic acid with an glucosaminylated nucleotide at the same position(s). Endonucleases that may be used include, for example, AbaSI, AbaAI, AbaCI, AbaDI, AbaTI, AbaUI, AcaPI, and/or PxyI. An adapter molecule can then be ligated to the cleaved end of the endonuclease reaction product, facilitating the subsequent purification, amplification or sequencing of the nucleic acid.

Accordingly, in one embodiment the invention provides a method for differentiating a 5-mC from 5-hmC in a genome or genome fragment. The genome or genome fragment may, for example, be mammalian in origin, such as a human genome or genome fragment. The method includes reacting the isolated genome or genome fragment containing 5-mC and 5-hmC with (i) UDP-GlcN in the presence of a glycosyltransferase catalyzing transfer of glucosamine to the 5-hmC; (ii) oxygenating any existing 5-mC residues to 5-hmC by the action of TET or mYOX1; (iii) reacting the newly created 5-hmC sites with UDP-Glc in the presence of a glycosyltransferase catalyzing transfer of glucose to the 5-hmC; (iv) cleaving the glucosylated template with a modification-dependent endonuclease that recognizes at least one of the modified nucleotides; and (v) differentiating the original 5-mC from the 5-hmC by an altered cleavage pattern.

In this embodiment, the oxygenation of any existing 5-mC residues to 5-hmC can be done in the presence of UDP-Glc and a glycosyltransferase to catalyze the transfer of glucose to 5-hmC as it is being formed from 5-mC. Alternatively, reaction conditions such as pH of the oxygenation reaction can be selected to optimize the yield of 5-hmC. See, for example, Ser. No. 13/827,087, "Compositions and Methods for Oxygenation of Nucleic Acids Containing 5-Methylpyrimidine," filed on the same date as the present application and hereby incorporated by reference in its entirety.

In another embodiment, the invention provides a method for differentiating a 5-mC from one or more of its oxidation products in a genome or genome fragment containing 5-mC and 5-hmC. The method includes reacting the isolated genome or genome fragment with UDP-2-glucosamine in the presence of a β-glycosyltransferase (BGT) catalyzing the transfer of 2-glucosamine to the 5-hmC; reacting the isolated genome or genome fragment with mYOX1 or TET or a chemical oxidizing agent and optionally with a reducing agent; cleaving the template with a modification dependent endonuclease that is capable of selectively cleaving a 5-hmC and not a 5-glucosaminated hydroxymethylcytosine; and differentiating the 5-mC from one or more of its oxidation products by an altered cleavage pattern.

The invention also provides preparations useful for converting methylcytosine or an oxidized nucleotide, such as 5-fC or 5-caC, or to a glucosylated nucleotide. The preparations include a reducing agent, such as $NaBH_4$, or an oxidizing agent, such as mYOX1, a TET enzyme, or an inorganic oxidizing agent such as $KRuO_4$; a glycosyltransferase, such as an α-glycosyltransferase or a β-glycosyltransferase; a UDP-GlcN or a UDP derivative, such as UDP-Glc or UDP-azido-glucose.

The invention also provides preparations useful for modifying and selectively cleaving nucleic acids. The preparations include a glycosyltransferase and an endonuclease having an amino acid sequence at least 95% identical to an enzyme such as AbaSI, AbaAI, AbaCI, AbaDI, AbaTI, AbaUI, AcaPI, and/or PxyI. The preparations also include (a) UDP-Glc and an oxidizing agent, or (b) UDP-GlcN. Where UDP-GlcN is included, the glycosyltransferase may be a BGT to catalyze the transfer of glucose to hydroxymethylated pyrimidine residues. Where UDP-Glc and an oxidizing agent are included, the oxidizing agent, which may be a methylcytosine oxygenase such as mYOX1 or a TET enzyme or may be an inorganic oxidizing agent such as $KRuO_4$, promotes the conversion of methylcytosine residues in a nucleic acid to hydroxymethylcytosine, which can be glucosylated by the combination of UDP-Glc and the glycosyltransferase, and can be recognized by the endonuclease.

The invention also provides kits useful for making these preparations and practicing these methods. For example, kits for modifying formylcytosine or carboxycytosine residues in a nucleic acid can include a reducing agent, such as sodium borohydride, permitting the reduction of formylcytosine or carboxycytosine residues to hydroxymethylcytosine; a glycosyltransferase (such as a β-glycosyltransferase); and a UDP derivative, such as UDP-Glc and/or UDP-azidoglucose (such as UDP-6-azidoglucose), permitting the transfer of a sugar or modified sugar to the hydroxymethylcytosine. These kits may also include an oxidizing agent (e.g., a methylcytosine oxygenase such as mYOX1 or a TET enzyme or an inorganic oxidizing agent such as KRuO$_4$) to promote the conversion of methylcytosine residues in a nucleic acid to hydroxymethylcytosine; UDP-GlcN; a restriction endonuclease (e.g., having an amino acid sequence at least 95% identical to AbaSI, AbaAI, AbaCI, AbaDI, AbaTI, AbaUI, AcaPI, and/or PxyI); or any combination of the above.

Kits for selectively modulating the susceptibility of modified nucleic acid residues to cleavage can include UDP-Glc; UDP-GlcN; a β-glycosyltransferase; and a reducing (e.g. sodium borohydride) or oxidizing agent (e.g., a methylcytosine oxygenase such as mYOX1 or a TET enzyme or an inorganic oxidizing agent such as KRuO$_4$).

Kits useful for modifying and selectively cleaving nucleic acids can include, for example, a glycosyltransferase and an endonuclease having an amino acid sequence at least 95% identical to an enzyme such as AbaSI, AbaAI, AbaCI, AbaDI, AbaTI, AbaUI, AcaPI, and/or PxyI. These kits can also include (a) UDP-Glc and an oxidizing agent, and/or (b) UDP-GlcN.

Some embodiments of the kits or preparations of the present invention include an optional nucleic acid, such as a nucleic acid that is to be modified, that is undergoing modification, and/or a control nucleic acid. Accordingly, a nucleic acid, if present, may include 5-hmC, 5-gmC, 5-gNmC, 5-fC, 5-caC, 5-mC, or any combination of the above.

DETAILED DESCRIPTION OF EMBODIMENTS

Endonucleases have been identified from bacteria and more will undoubtedly be discovered using routine BLAST searches based on the present disclosure that are capable of preferentially cleaving 5-β-gmC compared to C, 5-mC and 5-β-2-gNmC. In one example, the ZZYZ family members for example AbaSI (see for example WO 2011/091146), isoschizomers and mutants thereof preferentially cleave 5-β-gmC compared to C, 5-mC and 5-β-2-gNmC. For example, AbaSI has cleavage activity at 5-β-gmC that is 500 fold greater than 5-mC and 5-α-gmC. 5-β-gmC is the product of BGT mediated transfer of glucose from UDP-Glc to 5-hmC.

Figure 1:
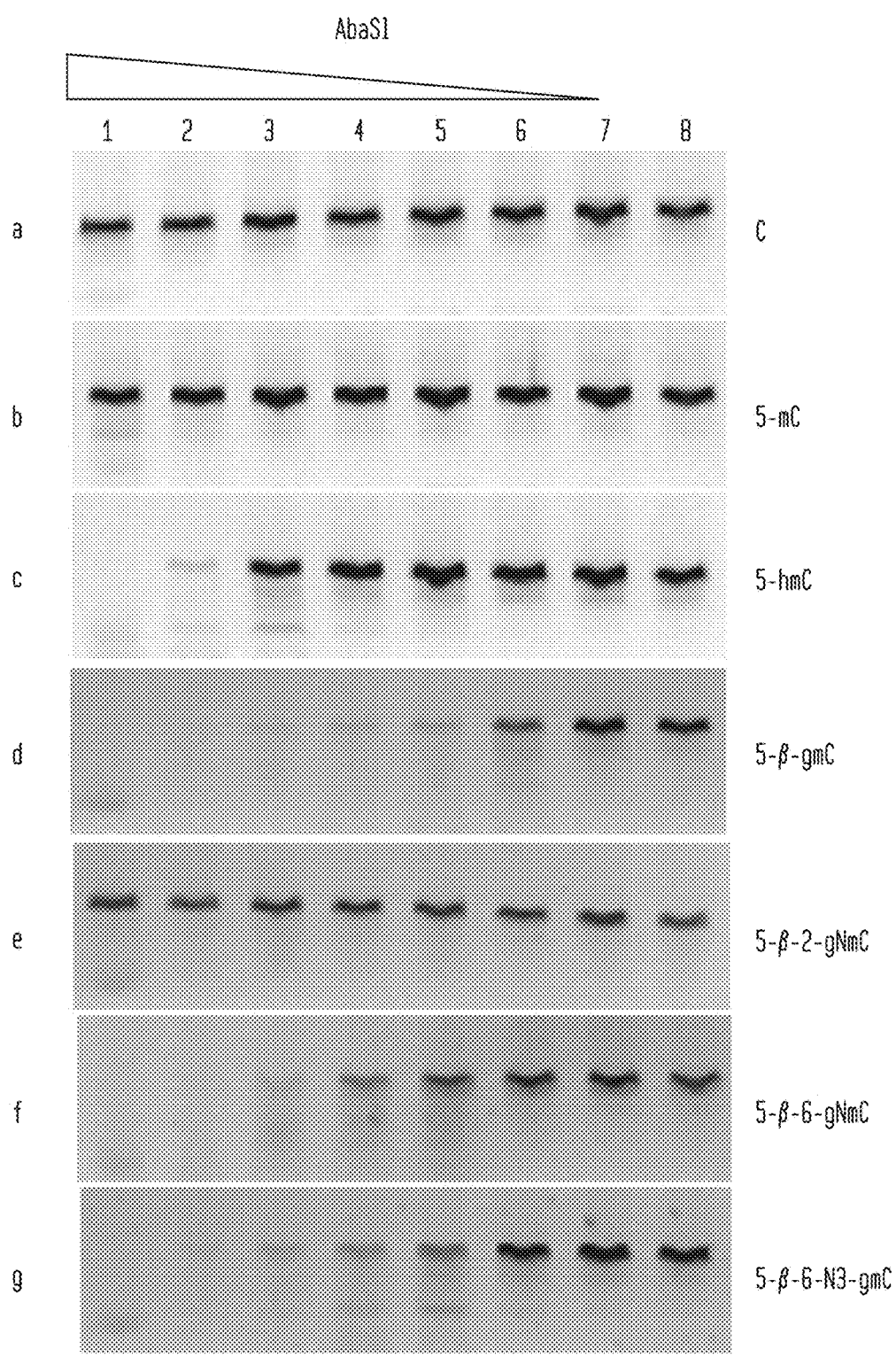
FIG. 1 shows that AbaSI recognizes 5-(β-glucosyloxymethyl)cytosine (5-β-gmC) but not 5-(β-2-glucosaminyloxymethyl)cytosine (5-β-2-gNmC) with high specificity as compared to 5-mC and C. The different forms of cytosine modification (panels a-g) were digested by a 10-fold serial dilution of AbaSI enzyme (lane 1 to lane 7, lane 8 is undigested control).

The specificity of AbaSI is demonstrated in the data shown in FIG. 1. AbaSI cleaves recognizes nucleic acids containing certain cytosine modifications, cleaving them a short distance from those modifications. Ten-fold serial dilutions of AbaSI were combined with a PCR product containing cytosine ("C," panel a), 5-methylcytosine ("5-mC," panel B), 5-hydroxymethylcytosine ("5-hmC," panel C), 5-(β-glucosyloxymethyl)cytosine ("5-β-gmC," panel D), 5-(β-2-glucosaminyloxymethyl)cytosine ("5-β-2-gNmC," panel E), 5-(β-6-glucosaminyloxymethyl)cytosine ("5-β-6-gNmC," panel F), or 5-(β-6-azidoglucosyloxymethyl)cytosine ("5-β-6-N3gmC," panel G). The PCR products containing 5-β-gmC, 5-β-2-gNmC, 5-β-6-gNmC, or 5-β-6-N3gmC were generated by treatment of 5-hmC PCR DNA (panel c) with T4-β-glucosyltransferase (BGT) and the corresponding UDP-sugar (uridine diphospho-glucose (UDP-Glc), UDP-2-glucosamine (UDP-2-GlcN), UDP-6-glucosamine (UDP-6-GlcN), and UDP-6-N3-Glc, respectively). The results show that AbaSI does not digest C and 5-mC even at high concentrations (panels a and b) whereas AbaSI can digest 5-β-gmC even at very low concentrations (panel d). With respect to the three glucosylated or glucosaminated cytosines, AbaSI can digest 5-β-6-gNmC and 5-β-6-N3gmC (panels f and g) more efficiently than it digests 5-hmC (although less efficiently than it digests 5-β-gmC. In contrast, it does not digest 5-β-2-gNmC (panel e).

Figure 2:
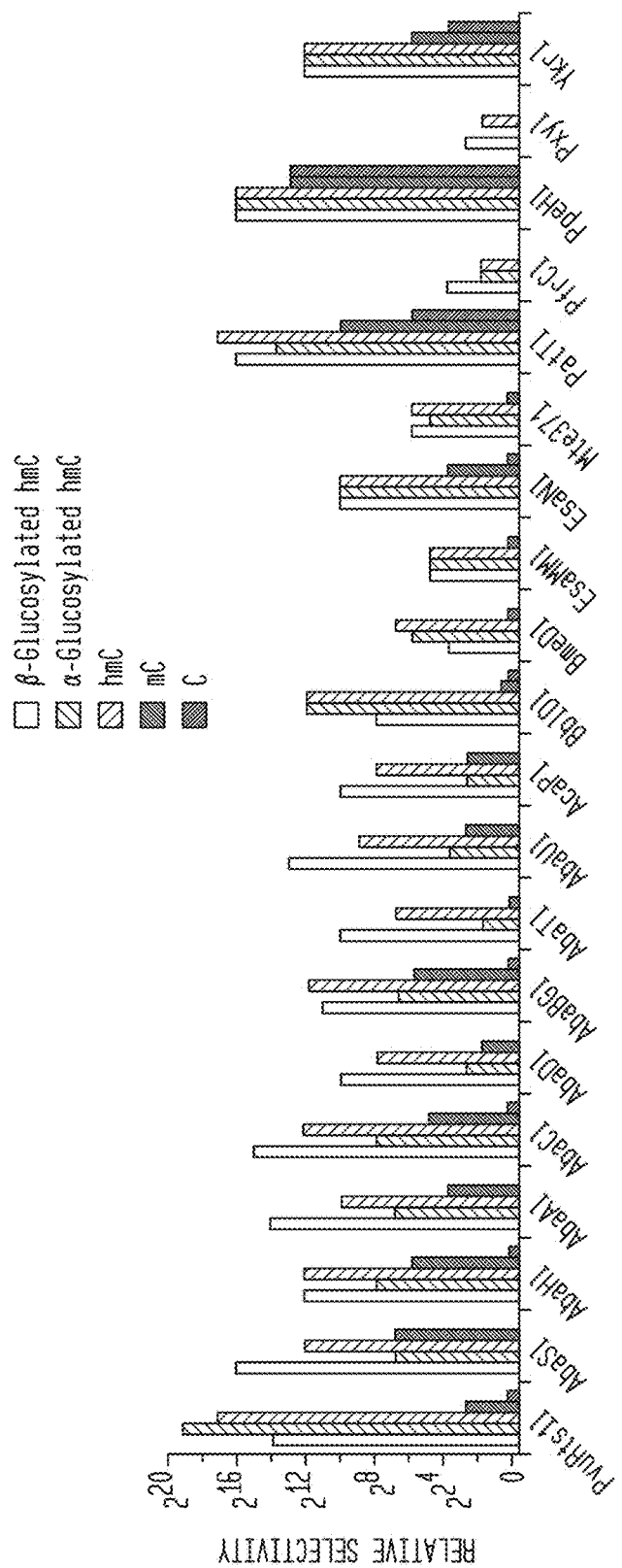
FIG. 2 depicts the relative selectivity of a variety of endonucleases for nucleic acid substrates containing 5-β-gmC ("β-glucosylated hmC"), 5-α-gmC ("α-glucosylated hmC"), 5-hydroxymethylcytosine ("hmC"), 5-methylcytosine ("mC"), or unmodified cytosine ("C").

Other endonucleases that differentiate between various forms of modified cytosine are also available, such as other ZZYZ family members described in WO 2011/091146 and enzymes described in Borgaro et al. (2013) "Characterization of the 5-hydroxymethylcytosine-specific DNA restriction endonucleases," Nucleic Acids Research, doi: 10.1093/nar/gkt102, the entire disclosures of each of which are incorporated herein by reference. Several endonucleases that discriminate among various cytosine modifications are described in FIG. 2. For example, PvuRts1I cleaves nucleic acids containing hydroxymethylcytosine or glucosyloxymethylcytosine far more efficiently than it cleaves nucleic acids containing only methylcytosine or unmodified cytosine. AbaSI, as described in the preceding paragraph, cleaves nucleic acids containing 5-β-gmC more efficiently than it cleaves nucleic acids containing 5-hmC, which are nevertheless cleaved more efficiently than those nucleic acids containing only 5-mC or unmodified cytosine. Like AbaSI, AbaAI, AbaCI, AbaDI, AbaTI, AbaUI, AcaPI, and PxyI all demonstrate increased specificity for nucleic acids containing 5-β-gmC compared to nucleic acids containing only 5-hmC. Accordingly, for any of these enzymes β-glucosylation of hydroxymethylcytosine can be used as an "on switch" to promote cleavage near those positions, whereas β-glucosylation could be used as an "off switch" for enzymes such as PvuRts1I, AbaBGI, BbiDI, BmeDI, or PatTI. On the other hand, α-glucosylation of 5-hmC generates a more efficient substrate for PvuRts1I, and could be used as an "on switch" to target cleavage events to those locations in a nucleic acid.

It is expected that the use of endonucleases with preferential specificity for a specific modified nucleotide over other modified and unmodified nucleotides can be detected using the method described herein for 5-mC, 5-hmC, 5-fC, and 5-caC. In combination with the cofactor UDP-Glc, this system enables sequencing different epigenetic states of 5-mC and greatly enhances the ability to determine the epigenetic modification at a single base resolution level.

An embodiment of the method relies on modifying the non-target modified base (for example, 5-hmC) chemically and/or enzymatically in such a way that its reactivity to a endonuclease is completely or partially blocked, and then chemically or enzymatically reacting the target modified base to convert it into a newly formed 5-hmC (e.g., with a reducing or oxidant agent) which can be then be reacted with a glycosyltransferase to form 5-gmC which in turn can be cleaved by an endonuclease that recognizes 5-gmC preferentially in a positive identification.

By the appropriate choice of the substrate for modifying the non-target and target modified bases, this invention provides an on-off switch assay which is determined by enzyme specificity. For example, if in the first step UDP-2-GlcN is used to label pre-existing 5-hmC sites (resulting in an off-signal for AbaSI cleavage), and in the second step the sample is treated with a methylpyrimidine oxygenase (mYOX), BGT and UDP-Glc, an "on-signal" for AbaSI cleavage will be generated exclusively for 5-mC sites which underwent oxidation by mYOX. If UDP-Glc is used to label pre-existing 5-hmC sites (on-signal for AbaSI cleavage), and the sample is treated with an mYOX, BGT and UDP-2-GlcN, then an "off-signal" will be generated for all 5-mC sites which were converted into 5-hmC by mYOX-mediated oxidation.

The 5-mC may be chemically or enzymatically converted to 5-hmC by reacting the 5-mC with mYOX1 (see for example, "nMCO1" described in U.S. Provisional Application No. 61/723,427), TET enzymes or chemical oxidizing agents. Similarly, oxidation of 5-mC to 5-hmC to 5-fc to 5-CaC can be achieved by chemical or enzymatic oxidation using mYOX1 or TET. Specific chemical oxidation of 5-hmC to 5-fC in synthetic nucleotide oligomer single strand (ssDNA) containing 5-hmC can be achieved with potassium perruthenate, $KRuO_4$ (Booth, et al. Science, 336:934-937 (2012)). $KRuO_4$ can oxidize 5-hmC in double-stranded DNA (dsDNA), with an initial denaturing step before the addition of the oxidant, resulting in quantitative conversion of 5-hmC to 5-fC. Other oxidants known in art, such as Osmium (VIII)-based oxidants, Cerium (IV)-based oxidants, and Chromium (VI)-based oxidants may be used for the oxidation of 5-hmC to 5-fC.

Figure 3:
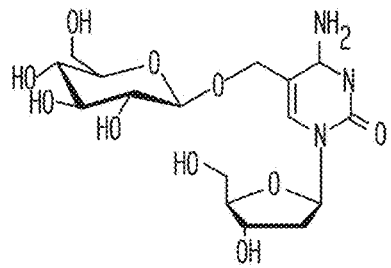
FIG. 3 depicts selected cytosine modifications that can be achieved through the addition of glucose, modified glucose, or glucosamine residues by T4-BGT alone or in combination with β-glucosyl-α-glycosyltransferase from bacteriophage T6 ("T6-BGAGT").
Figure 3:
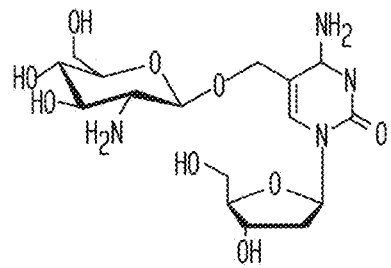
Figure 3:
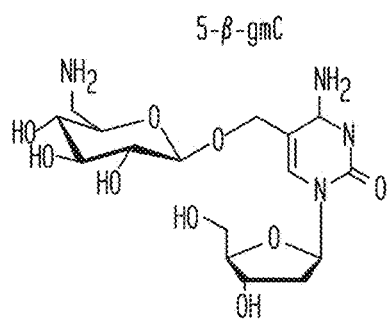
Figure 3:
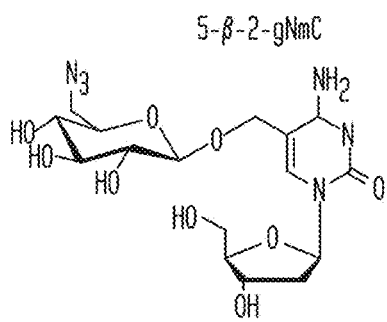
Figure 3:
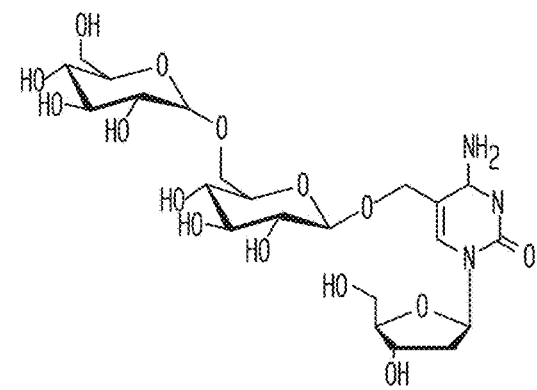
Figure 3:
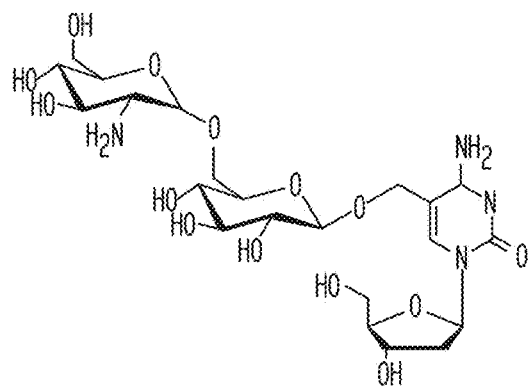
Figure 3:
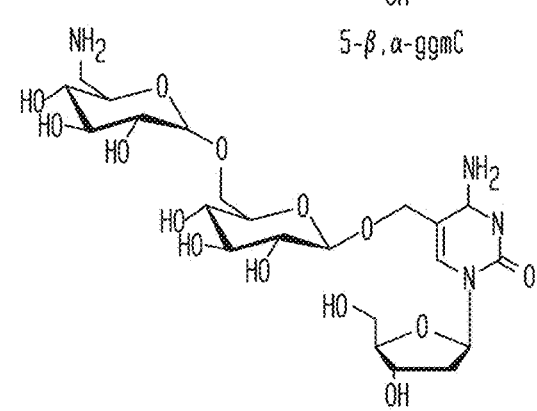
Figure 3:
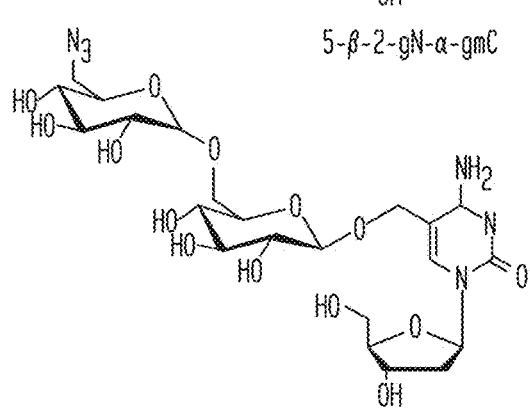

A variety of sugars and modified sugars can be used to alter the propensity of a 5-hmC to trigger an endonuclease-mediated cleavage event. Some of these sugars and modified sugars are depicted in FIG. 3. For example, T4-BGT can be used to add glucose, 2-glucosamine, 6-glucosamine, or 6-azidoglucose to 5-hmC. T4-BGT can also be used in combination with a β-glucosyl-α-glycosyltransferase, such as the one from bacteriophage T6, to generate disaccharidyl cytosine modifications as shown in FIG. 3. By controlling the modifications made to a particular nucleobase, the properties of that nucleobase can be changed in a manner facilitating its discrimination, whether through changes in its reactivity with an endonuclease; changes in the kinetics of synthesis of a complementary nucleic acid; or directly measured changes in size, shape, or charge density.

Figure 7:
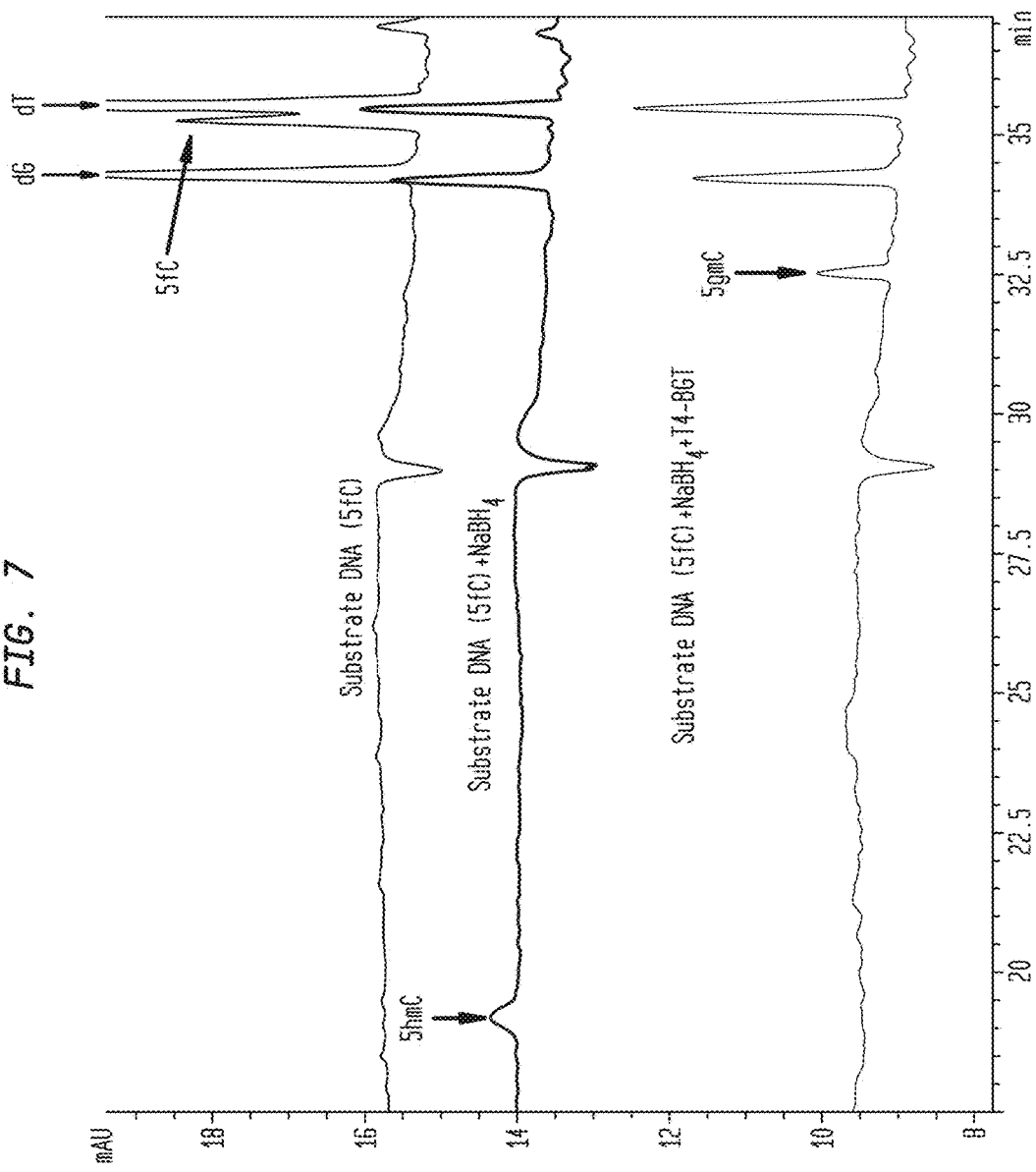
FIG. 7 depicts LC-MS analyses of a nucleic acid containing 5-fC (top trace) and the same nucleic acid after treatment with 100 mM sodium borohydride (middle trace) or with sodium borohydride, UDP-Glc, and T4-BGT (bottom trace).

The reduction of 5-fC and its conversion to 5-β-gmC was demonstrated in the experiment depicted in FIG. 7. Specifically, FIG. 7 is an LC-MS analysis of a nucleic acid originally including 5-fC (top trace). In the presence of sodium borohydride ($NaBH_4$), the 5fC is converted to 5-hmC (middle trace). When UDP-Glc and a BGT such as T4-BGT were also provided, the 5-fC was converted all the way to 5-β-gmC, confirming that the modified forms of cytosine can be interconverted, facilitating their subsequent detection and discrimination.

In one embodiment the method comprises one or more of the following steps;
(a) Genomic DNA is treated with BGT and UDP-2-GlcN, so that all 5-hmC residues are converted to 5-β-2-gNmC.
(b) (i) The resulting DNA is treated with mYOX1, a Tet enzyme or a chemical oxidant agent (converts 5-mC to 5-hmC), BGT and UDP-Glc, so that all existing 5-mC residues are converted to 5-β-gmC; or
(ii) The resulting DNA is treated with a reducing agent (e.g., $NaBH_4$, converts 5-fC to 5-hmC), BGT and UDP-Glc to generate 5-β-gmC; or
(iii) The resulting DNA is treated with a reducing agent (e.g., $NaBH_4$, converts 5-fC to 5-hmC), BGT and UDP-2-GlcN, so that all 5-fC residues are converted to 5-β-2-gNmC. Then, the resulting DNA is treated with a second reducing agent (a different reducing agent or the same reducing agent but in the presence of certain additives that converts 5-caC to 5-hmC), BGT, and UDP-Glc to generate 5-β-gmC.
(c) (i) The DNA is digested with a 5-β-gmC-dependent endonuclease such as AbaSI, which cleaved at a fixed distance from 5-β-gmC and left a sticky end (2-base 3'-overhang). Since the endonuclease does not recognize C or 5-β-2-gNmC no cleavage associated with these sites occurs. The only sticky ends created are those resulting from 5-β-gmC residues, which in turn are exclusively associated to 5-mC sites; or
(ii) The DNA is digested with endonuclease, which cleaves 5-β-gmC exclusively associated to 5-fCs sites, but not 5-β-2-gNmC, 5-mC, or C, leaving a sticky end (2-base 3'-overhang).
(iii) the DNA is digested with endonuclease, which cleaves 5-β-gmC exclusively associated to CaC sites, but not 5-β-2-gNmC, 5-mC, or C, leaving a sticky end (2-base 3'-overhang).
(d) A first adaptor (e.g., biotinylated adaptor A) is then ligated onto the cleaved ends.
(e) The ligated DNA is then subjected to random fragmentation to about 200 bp.
(f) Beads may be used to pull out the fragments with the ligated adaptor. For example, avidin beads may be used to pull out the biotin labeled adaptor (adaptor A). A person of ordinary skill in the art will recognize other affinity systems and immobilization matrices that can be used in place of biotin/avidin beads.
(g) After polishing the ends, adaptor P is then ligated onto the DNA fragments on the beads.
(h) The adaptor-specific PCR and the adapter ligated DNA enters the library preparation pipeline for specific sequencing platform where the end-sequencing is done from the adaptor A.

Reducing agents and conditions can be used herein that can convert the carboxylic acids into alcohols, e.g., $NaBH_4$, $CoCl_2$, i-$Pr_2NH$, EtOH/$H_2O$ (Jagdale, et al. *Synthesis*, 660-664 (2009)); EDC, HOBt, $NaBH_4$, THF/$H_2O$ (Morales-Serna, et al. *Synthesis*, 1375-1382 (2011)); and cyanuric chloride, $NaBH_4$, NMM/$H_2O$ (Falorni, et al. *Tetrahedron*

Lett., 4395-4396 (1999)) as well as other reducing agents known to a person of ordinary skilled in the art.

Indeed, many water-soluble metal or metalloid hydrides are able to reduce aldehydes and/or carboxylic acids to alcohols. Examples of such reducing agents are sodium borohydride and related compounds where from 1 to 3 of the hydrogens are replaced by other moieties, such as cyano and alkoxy containing up to about 5 carbon atoms. Examples of substituted borohydrides, all of which are sodium, potassium, or lithium salts, include cyanoborohydride, dicyanoborohydride, methoxyborohydride, dimethoxyborohydride, trimethoxyborohydride, ethoxyborohydride, diethoxyborohydride, triethoxyborohydride, propoxyborohydride, dipropoxyborohydride, tripropoxyborohydride, butoxyborohydride, dibutoxyborohydride, tributoxyborohydride, and so forth. Examples of other water-soluble metal hydrides include lithium borohydride, potassium borohydride, zinc borohydride, aluminum borohydride, zirconium borohydride, beryllium borohydride, and sodium bis(2-methoxyethoxy)aluminium hydride. Sodium borohydride can also be used in combination with a metal halide, such as cobalt(II), nickel(II), copper(II), zinc(II), cadmium (II), calcium (II), magnesium(II), aluminum(III), titanium (IV), hafnium(IV), or rhodium(III), each of which can be provided as a chloride, bromide, iodide, or fluoride salt. Alternatively, sodium borohydride can be used in combination with iodine, bromine, boron trifluoride diethyl etherate, trifluoroacetic acid, catechol-trifluoroacetic acid, sulfuric acid, or diglyme. Particular reducing strategies include the combination of potassium borohydride with lithium chloride, zinc chloride, magnesium chloride, or hafnium chloride; or the combination of lithium borohydride and chlorotrimethylsilane. Other reducing strategies include the use of borane, borane dimethyl sulfide complex, borane tetrahydrofuran complex, borane-ammonia complex, borane morpholine complex, borane dimethylamine complex, borane trimethylamine complex, borane N,N-diisopropylethylamine complex, borane pyridine complex, 2-picoline borane complex, borane 4-methylmorpholine complex, borane tert-butylamine complex, borane triphenylphosphine complex, borane N,N-diethylaniline complex, borane di(tert-butyl)phosphine complex, borane diphenylphosphine complex, borane ethylenediamine complex, or lithium ammonia borane. Alternative reducing strategies include the reduction of carboxylic acids via the formation of hydroxybenzotriazole esters, carboxy methyleniminium chlorides, carbonates, O-acylisoureas, acyl fluorides, cyanurates, mixed anhydrides, arylboronic anhydrides, acyl imidazolide, acyl azides, or N-acyl benzotriazoles, followed by reaction with sodium borohydride to give the corresponding alcohols.

In one embodiment, 5-hmC sequencing can use BGT and UDP-Glc to generate AbaSI-active 5-β-gmC sites, and T4-α-glucosyltransferase (AGT) and UDP-Glc to generate AbaSI-inactive 5-α-gmC sites as a negative control. In another embodiment, 5-hmC sequencing can use BGT and UDP-Glc to generate the AbaSI-active 5-β-gmC sites, and BGT and UDP-2-GlcN to generate AbaSI-inactive 5-β-2-gNmC as a negative control for 5-hmC.

In one embodiment, newly generated 5-hmC sites can be differentiated from pre-existing 5-hmC sites by sequentially transferring distinct sugar moieties from UDP-2-GlcN or native UDP-Glc using BGT.

In a further embodiment of the invention, UDP-Glc modified by any of keto, thiol, chloro, fluoro, bromo, iodo, nitro, boron, and other substituents may be transferred onto 5-hmC using BGT and may block AbaSI activity. Keto, thiol, chloro, fluoro, bromo, iodo, nitro, boron, and other substituents modifying glucose containing 5-hmC residues in a nucleic acid may facilitate cytosine modification mapping and inhibit AbaSI cleavage.

All references cited herein are incorporated by reference.

EXAMPLES

Example 1: Mapping of 5-hmC in a Nucleic Acid Sequence

The locations of 5-hmC in a nucleic acid sample can be determined using differential cleavage.

A BGT can transfer glucose ("Glc") from UDP-Glc to 5-hmC to form the glucoylated residue 5-β-2-gmC. Glucosylation enhances the sensitivity of the nucleic acid to a glucosylation-sensitive restriction enzyme such as AbaSI (see FIG. 2). Accordingly, the identification of 5-hmC sites in a sample can be facilitating by glucosylating the nucleic acid, followed by identifying the locations of AbaSI cleavage sites.

Example 2: Exclusive 5-mC Methylome Mapping

Figure 4:
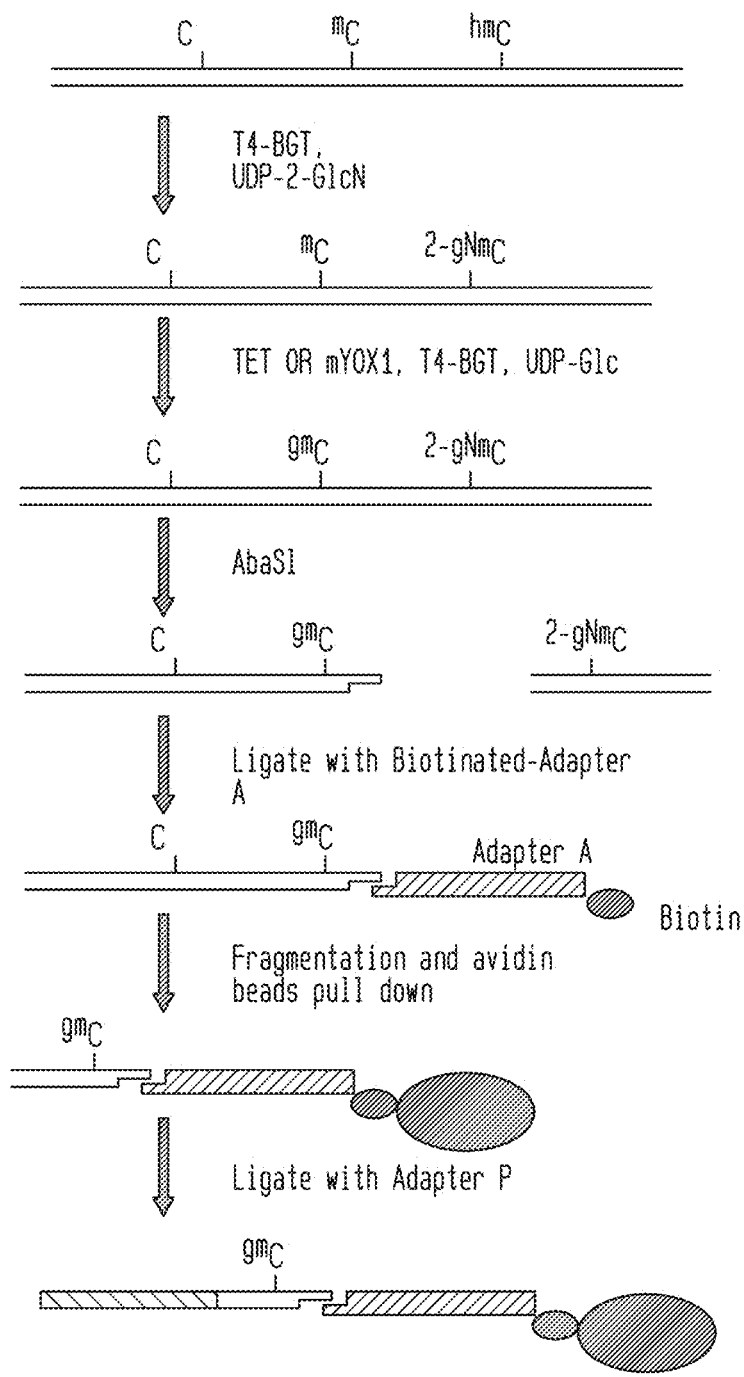
FIG. 4 depicts one example of an assay for detecting and/or mapping 5-mC.

An exemplary process for mapping 5-mC residues in a nucleic acid is depicted in FIG. 4.

As shown in FIG. 4, genomic DNA is treated with a BGT and UDP-2-glucosamine, converting 5-hmC residues to 5-β-2-gNmC. The resulting DNA is treated with a methylpyrimidine oxygenase from Neisseria (mYOX1), TET or a chemical oxidizing agent, BGT and UDP-Glc, converting existing 5-mC residues to 5-β-gmC. The DNA is digested with a 5-β-gmC-dependent restriction enzyme, such as AbaSI, cleaving at a fixed distance from 5-β-gmC and leaving a sticky end (2-base 3'-overhang). Since AbaSI does not recognize C or 5-β-2-gNmC, the only sticky ends created are those resulting from 5-β-gmC residues, which in turn are exclusively associated to 5-mC sites. A biotinylated adaptor A is then ligated onto the cleaved ends. The ligated DNA is then subjected to random fragmentation to an average size of about 200 bp. Avidin beads are used to pull out the fragments with the ligated adaptor A. After polishing the ends, adaptor P is then ligated onto the DNA fragments on the beads. The adaptor-specific PCR and the adapter ligated DNA enters the library preparation pipeline for specific sequencing platform where the end-sequencing is done from the adaptor A.

Bioinformatic analysis of the sequencing reads is facilitated by the presence of adapter A which marks the enzyme cleavage sites. After mapping the read back to the reference genome, the modified cytosine can be mapped at fixed distance away from the cleavage sites.

Example 3: Exclusive 5-fC and/or 5-caC Mapping

Figure 5A:
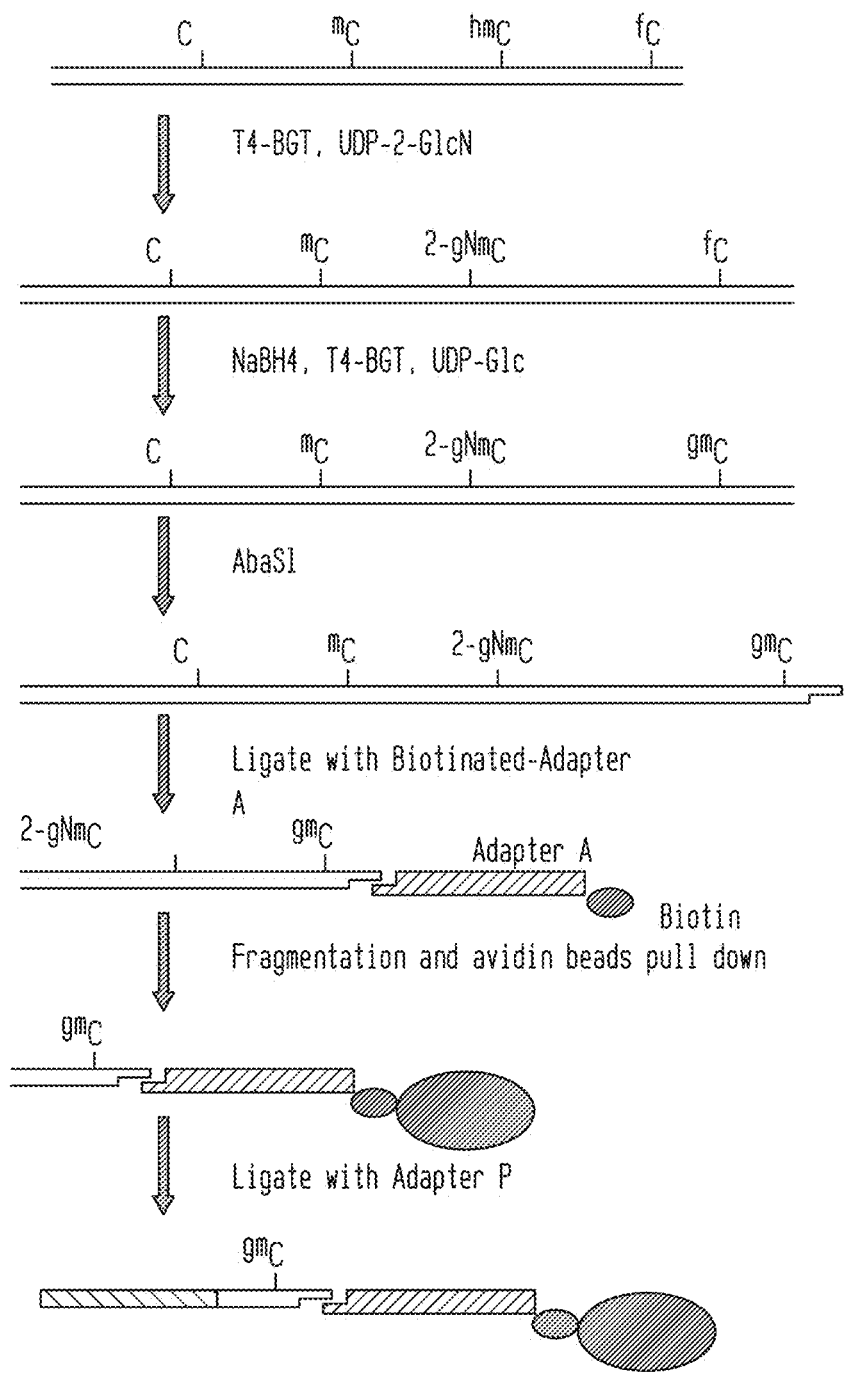
FIG. 5A-B depicts two examples of assays for detecting and/or mapping 5-fC. The assay in FIG. 5A includes a step involving glucosylating hydroxymethylcytosine residues newly-formed from the reduction of 5-fC. The assay in FIG. 5B includes a step involving azidoglucosylating hydroxymethylcytosine residues newly-formed from the reduction of 5-fC.
Figure 5B:
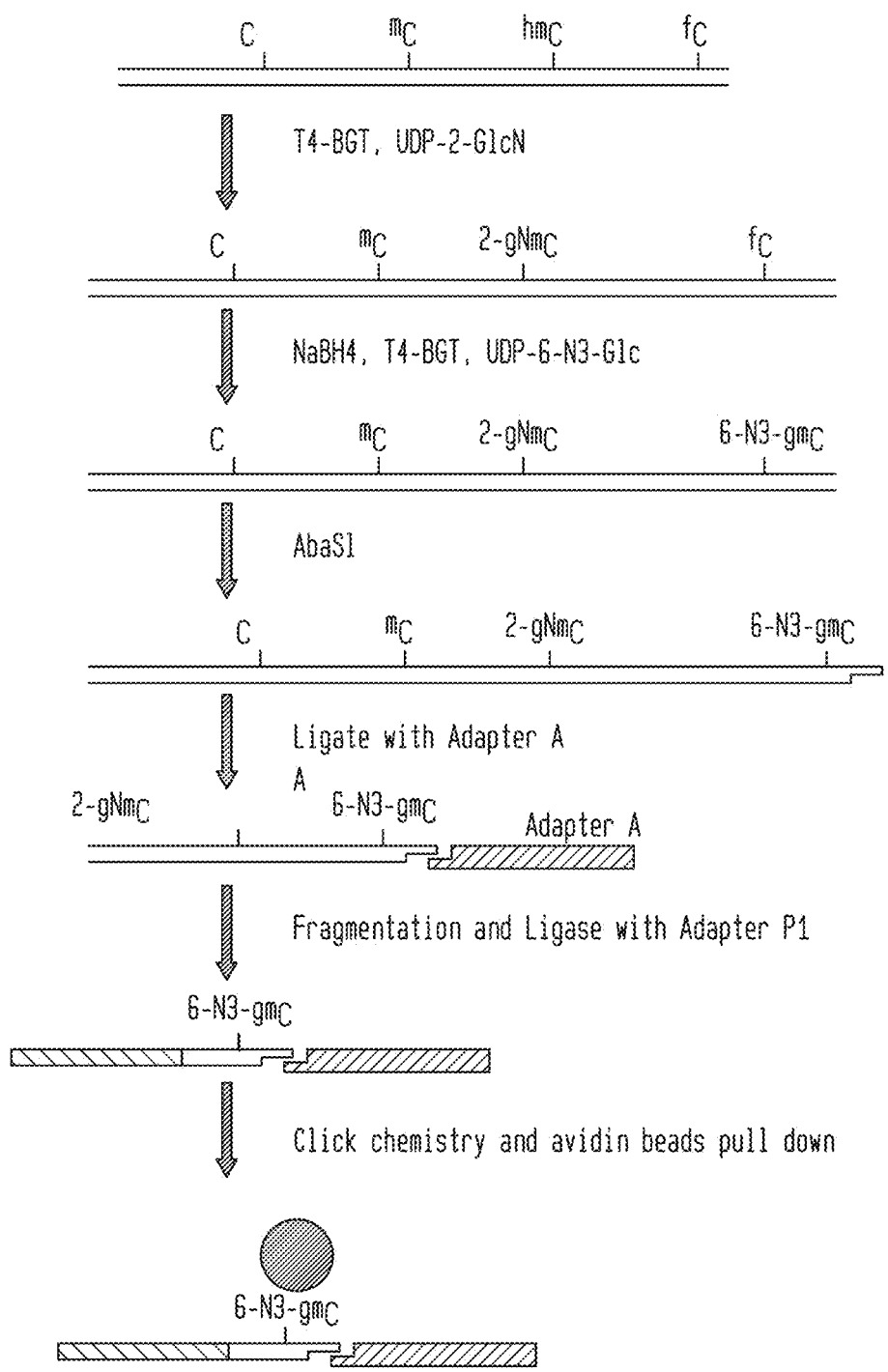

Exemplary processes for identifying 5-fC or 5-caC residues in a nucleic acid are depicted in FIGS. 5A and 5B.

Example 3A: Glucosamination

As shown in FIG. 5A, a BGT can be used to catalyze the addition of 2-glucosamine from UDP-2-GlcN to a 5-hmC residue, converting those residues to 5-β-2-gNmC. A reducing agent such as $NaBH_4$ (optionally in the presence of additives), can be used to reduce 5-fC and/or 5-caC to 5-hmC. The newly formed 5-hmC when combined with BGT and UDP-Glc can be subsequently converted to 5-β-gmC.

As described in Example 2, the DNA is digested with a 5-β-gmC-dependent restriction enzyme, such as AbaSI, cleaving at a fixed distance from 5-β-gmC and leaving a sticky end (2-base 3'-overhang). Since AbaSI does not recognize C or 5-β-2-gNmC, the only sticky ends created are those resulting from 5-β-gmC residues, which in turn are exclusively associated to 5-fC and/or 5-caC sites. A biotinylated adaptor A is then ligated onto the cleaved ends. The ligated DNA is then subjected to random fragmentation to an average size of about 200 bp. Avidin beads are used to pull out the fragments with the ligated adaptor A. After polishing the ends, adaptor P is then ligated onto the DNA fragments on the beads. The adaptor-specific PCR and the adapter ligated DNA enters the library preparation pipeline for specific sequencing platform where the end-sequencing is done from the adaptor A.

Bioinformatic analysis of the sequencing reads is facilitated by the presence of adapter A which marks the enzyme cleavage sites. After mapping the read back to the reference genome, the modified cytosine can be mapped at fixed distance away from the cleavage sites.

Example 3B: 6-Azido-Glucose

Another exemplary process for mapping the locations of 5-fC and/or 5-caC is shown in FIG. 5B. The process depicted in FIG. 5B, like the process depicted in FIG. 5A, begins with the addition of 2-glucosamine from UDP-2-GlcN to a 5-hmC residue, converting those residues to 5-β-2-gNmC in a reaction catalyzed by a BGT, and the subsequent reduction of 5-fC and/or 5-caC residues to newly-generated 5-hmC residues. In the method depicted in FIG. 5B, UDP-6-azido-glucose (UDP-6-N3-Glc) is added to those newly-generated 5-hmC residues by a BGT. The DNA is digested with a 5-β-gmC-dependent restriction enzyme, such as AbaSI, cleaving at a fixed distance from 5-β-gmC and leaving a sticky end (2-base 3'-overhang). Since AbaSI does not recognize C or 5-β-2-gNmC, the only sticky ends created are those resulting from the azidoglucosylated residues, which in turn are exclusively associated to 5-fC and/or 5-caC sites.

The sticky ends are ligated to an adapter A. The resulting DNA is fragmented and ligated to a second adapter P1. The azido moiety can derivatized with a biotin label via azide-alkyne Huisgen cycloaddition using a copper(I) catalyst ("click chemistry") or via copper-free variants (for example, using strained cyclooctyne derivatives) and avidin beads can then be used to selectively purify the fragments containing the azidoglucosylated residues.

Example 4: Exclusive 5-caC Mapping

Figure 6:
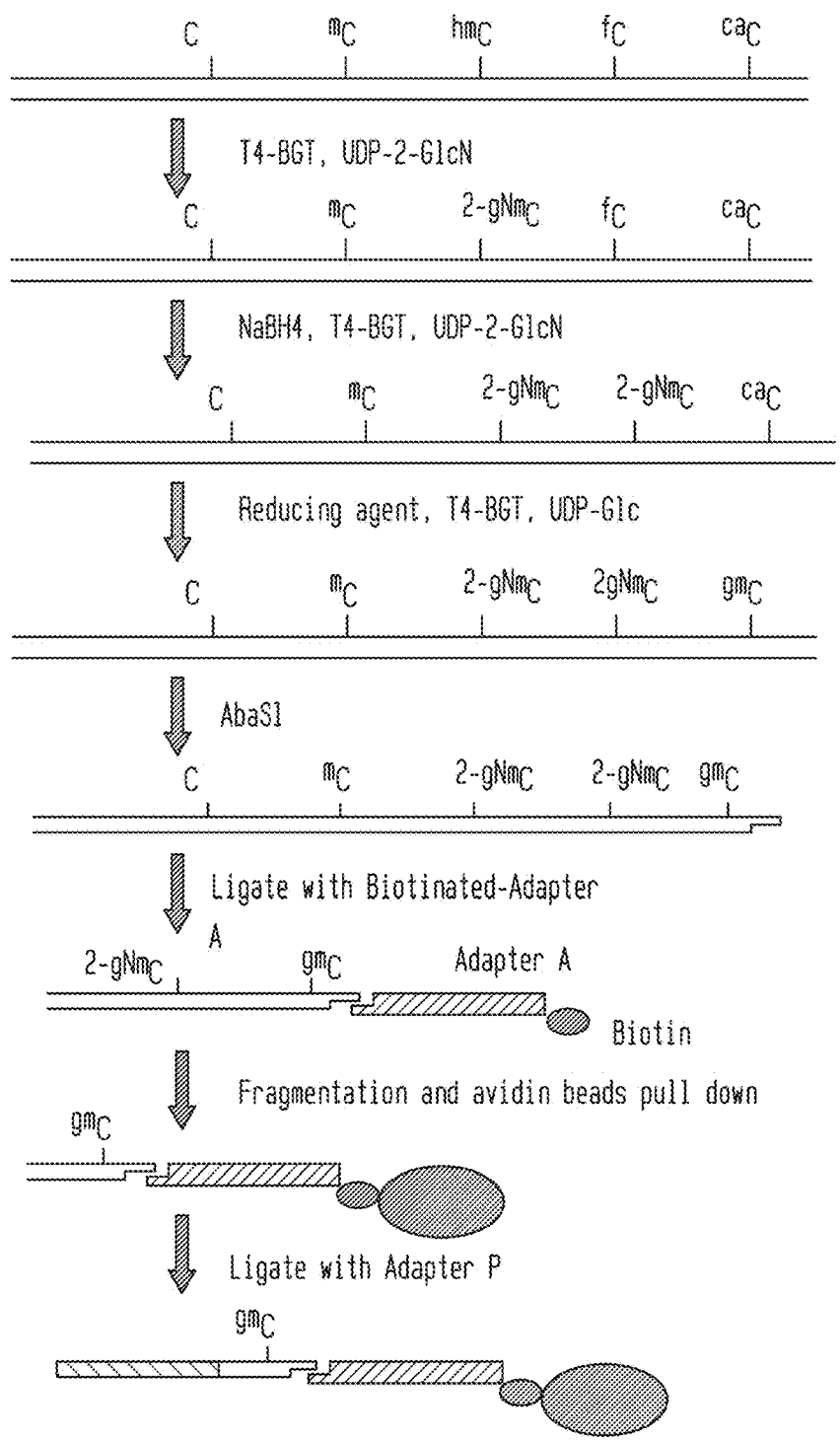
FIG. 6 depicts an example of an assay for detecting and/or mapping 5-caC.

An exemplary process for mapping the locations of 5-caC in a nucleic acid sample is provided in FIG. 6.

As shown in FIG. 6, genomic DNA is treated with BGT and UDP-2-GlcN, so that substantially all 5-hmC residues are converted to 5-β-2-gNmC. The resulting DNA is treated with a reducing agent (e.g., NaBH$_4$, converts 5-fC to 5-hmC), BGT and UDP-2-GlcN, so that all 5-fC residues are converted to 5-β-2-gNmC. Then, the resulting DNA is treated with a second reducing agent (a different reducing agent or the same reducing agent but in the presence of certain additives converts 5-caC to 5-hmC), BGT, and UDP-Glc to generate 5-β-gmC. The DNA is digested with a restriction endonuclease such as AbaSI, which cleaves 5-β-gmC exclusively associated to 5-caC sites but not 5-β-2-gNmC, 5-mC or C to leave a sticky end (2-base 3'-overhang). These sites are then identified through ligation to a biotinylated adapter, fragmentation and purification using avidin-associated beads, ligation and analysis as described in Example 2.

What is claimed is:

1. A method for selectively altering any modified cytosine in a nucleic acid that is hydroxymethylcytosine (hmC) or methylcytosine (mC), comprising:
    (a) reacting the nucleic acid with UDP-glucosamine in the presence of a glycosyltransferase to convert hmC in the nucleic acid to glucosaminylated cytosine, and
    (b) reacting the nucleic acid with an oxidizing agent and UDP-glucose to convert mC to glucosylated methylcytosine wherein the oxidizing agent is methyl cytosine oxygenase or $KRuO_4$.

2. The method according to claim 1, wherein the reaction with UDP-glucose is catalyzed by a glycosyltransferase.

3. The method according to claim 1, further comprising cleaving the nucleic acid with an endonuclease specific for the glucosylated nucleotides and not for glucosaminylated nucleotides.

4. The method according to claim 3, wherein the endonuclease has an amino acid sequence at least 95% identical to SEQ ID NO: 3.

5. The method according to claim 3, wherein the endonuclease has an amino acid sequence at least 95% identical to an enzyme selected from the group consisting of SEQ ID NOs: 3-8 and SEQ ID NO: 10.

6. The method according to claim 3, comprising: ligating an adapter to the cleaved end of the nucleic acid.

7. The method according to claim 1, wherein the methylcytosine oxygenase is a TET enzyme.

8. The method according to claim 1, wherein the methylcytosine oxygenase is mYOX1.

9. The method according to any one of claims 1-6, 7 and 8, comprising differentiating pre-existing 5-hydroxymethylcytosine from newly formed 5-hydroxymethylcytosine in a nucleic acid where 5-methylcytosine is a precursor of 5-hydroxymethylcytosine.

* * * * *